United States Patent
Maehara

(10) Patent No.: US 11,279,957 B2
(45) Date of Patent: Mar. 22, 2022

(54) METHOD FOR PRODUCING POLYESTER

(71) Applicant: MITSUBISHI GAS CHEMICAL COMPANY, INC., Chiyoda-ku (JP)

(72) Inventor: Akira Maehara, Niigata (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 0 days.

(21) Appl. No.: 16/642,604

(22) PCT Filed: Aug. 28, 2018

(86) PCT No.: PCT/JP2018/031776
§ 371 (c)(1),
(2) Date: Feb. 27, 2020

(87) PCT Pub. No.: WO2019/044837
PCT Pub. Date: Mar. 7, 2019

(65) Prior Publication Data
US 2020/0347416 A1   Nov. 5, 2020

(30) Foreign Application Priority Data
Aug. 29, 2017 (JP) .............................. JP2017-164469

(51) Int. Cl.
C12N 1/20 (2006.01)
C12P 7/625 (2022.01)

(52) U.S. Cl.
CPC .................................... C12P 7/625 (2013.01)

(58) Field of Classification Search
CPC ..................................................... C12P 7/625
See application file for complete search history.

(56) References Cited

U.S. PATENT DOCUMENTS

| | | | |
|---|---|---|---|
| 2012/0135480 A1 | 5/2012 | Nakas et al. | |
| 2014/0057326 A1 | 2/2014 | Sato et al. | |
| 2014/0342430 A1 | 11/2014 | Rahman et al. | |
| 2016/0237462 A1 | 8/2016 | Arikawa et al. | |

FOREIGN PATENT DOCUMENTS

| | | |
|---|---|---|
| EP | 0 052 459 A1 | 5/1982 |
| EP | 0 440 165 A2 | 8/1991 |
| EP | 2 910 641 A1 | 8/2015 |
| JP | 5-15383 A | 1/1993 |
| JP | 5-49487 A | 3/1993 |
| JP | 7-177876 A | 7/1995 |
| JP | 2015-523322 A | 8/2015 |
| JP | 2017-29082 A | 2/2017 |
| JP | 2017-99385 A | 6/2017 |
| WO | WO 2012/102371 A1 | 8/2012 |
| WO | WO 2012/174451 A1 | 12/2012 |
| WO | WO 2013/166469 A2 | 11/2013 |
| WO | WO 2014/032633 A1 | 3/2014 |
| WO | WO 2014/065253 A1 | 5/2014 |
| WO | WO 2017/033652 A1 | 3/2017 |

OTHER PUBLICATIONS

M.T. Record et al. "Responses of *E. coli* to osmotic stress: large changes in amounts of cytoplasmic solutes and water", TIBS 23: 143-148. (Year: 1998).*
English Translation of WO2017/033652 retrieved from https://patentscope.wipo.int/search/en/detail.jsf?docId=JP274739077&_cid=P20-KK49LZ-26611-1 on Jan. 19, 2021 (Year: 2017).*
International Preliminary Report on Patentability and Written Opinion dated Mar. 3, 2020, in PCT/JP2018/031776, 21 pages.
Anderson, A. J. et al., "Occurrence, Metabolism, Metabolic Role, and Industrial Uses of Bacterial Polyhydroxyalkanoates", Microbiological Reviews, vol. 54, No. 4, 1990, pp. 450-472.
Fontanille, M. et al., "formation of polymers of b-hydroxybutyric acid in bacterial cells and a comparison of the morphology of growth with the formation of polyethylene in the solid state", Recent Advances in Mechanistic and Synthetic Aspects of Polymerization, NATO ASI Series, vol. 215, 1987, pp. 293-314.
Kusaka, S. et al., "Molecular mass of poly[(R )-3-hydroxybutyric acid] produced in a recombinant *Escherichia coli*", Applied Microbiology and Biotechnology, 1997, vol. 47, pp. 140-143.
Valentin, H. E. et al., "Production of poly(3-hydroxybutyrate-co-4-hydroxybutyrate) in recombinant *Escherichia coli* grown on glucose", Journal of Biotechnology, vol. 58, 1997, pp. 33-38.
Yoon, S. C. et al., "Synthesis of Copolymeric PHA by Hydrogenophaga pseudoflava and Ralstonia eutropha H16 from Various Lactones and Their Microstructural Studies", Korean Journal of Applied Microbiology and Biotechnology, vol. 28, No. 2, 2000, pp. 71-79.
Koma, D. et al., "Know components of medium?", Seibutsu-kogaku, vol. 89, No. 4, 2011, pp. 195-199.
Azizi, N. et al., "Acid pretreatment and enzymatic saccharification of brown seaweed for polyhydroxybutyrate (PHB) production using *Cupriavidus necator*", International Journal of Biological Macromolecules, vol. 101, 2017, pp. 1029-1040.

(Continued)

*Primary Examiner* — Tekchand Saidha
(74) *Attorney, Agent, or Firm* — Oblon, McClelland, Maier & Neustadt, L.L.P.

(57) ABSTRACT

To provide a method for producing a polyester comprising at least a 3-hydroxybutyrate unit as a polymerization unit and having a high molecular weight and a narrow molecular weight distribution (that is, small Mw/Mn).
A method for producing a polyester comprising culturing a microorganism in a culture solution containing a carbon source and a nitrogen source, the polyester having a weight average molecular weight of 1,000,000 or greater and comprising at least a 3-hydroxybutyrate unit as a polymerization unit. The culture conditions include maintenance of an osmotic pressure of the culture solution from 200 mOsm to 900 mOsm during culture period, and maintenance of a nitrogen atom concentration of the culture solution at 0.30 g/L or greater during culture period.

6 Claims, 10 Drawing Sheets

(56) References Cited

OTHER PUBLICATIONS

Passanha, P. et al., "The use of NaCl addition for the improvement of polyhydroxyalkanoate production by *Cupriavidus necator*", Bioresource Technology, vol. 163, 2014, pp. 287-294.
Extended European Search Report dated Sep. 25, 2020 in corresponding European Patent Application No. 18849965.1, 9 pages.

* cited by examiner

METHOD FOR PRODUCING POLYESTER

TECHNICAL FIELD

The present invention relates to a method for producing a polyester at least comprising a 3-hydroxybutyrate unit as a polymerization unit.

BACKGROUND ART

Many microorganisms accumulate polyhydroxyalkanoates (PHAs) as energy source/carbon source reserve materials in their living system. It is well known that PHAs accumulate when nutrients such as nitrogen, phosphorus, sulfur, oxygen and magnesium are limited while carbon sources are sufficient. PHAs are thermoplastic polyesters that have been drawing attention as a biodegradable and biocompatible plastic, and many studies have been conducted (Non-Patent Document 1). At least 100 types of monomer units constituting PHAs are known, among which a notable example is poly-3-hydroxybutyrate (hereinafter abbreviated as "P(3HB)"), which comprises (R)-3-hydroxybutyrate (hereinafter abbreviated as "3HB"). (Non-Patent Document 1) Non-Patent Document 1 describes that the molecular weight of the PHA generally decreases in a later stage of culture.

Also, Non-Patent Document 2, which is a review article for research on production of P(3HB), describes that the molecular weight of P(3HB) decreases during its accumulation in culture in which phosphorus is limited.

As a method to increase the molecular weight, there is a method for producing an ultra high molecular weight P(3HB) by introducing a P(3HB) biosynthetic gene (phaCAB) extracted from a P(3HB) synthesizing bacterium *Cupriavidus necator* into *Escherichia coli* XL1-Blue having no PHA synthesis system/degradation system, and culturing the genetically modified bacterium at pH 6 (Non-Patent Document 3).

Typically, weight average molecular weight Mw of a wild-type strain P(3HB) that produces P(3HB) is said to be approximately from 500000 to 1500000, approximately from 200000 to 2000000, or approximately from 10000 to 3000000, and it is considered difficult to synthesize an ultra high molecular weight P(3HB) having a Mw of 3000000 or greater because a wild-type microorganism has a large number of degrading enzymes in its bacterial cell. Furthermore, P(3HB) is accumulated in microorganisms as an energy source and carbon source reserve material, and thus degradation and use of P(3HB) upon depletion of the carbon source have been examined for many microorganisms. However, some examples indicate simultaneous occurrence of synthesis and degradation of PHAs. Further, the physiological meaning of the simultaneous occurrence of synthesis and degradation of PHAs is still not clarified. Furthermore, the simultaneous occurrence of synthesis and degradation of PHAs in a PHA-producing wild-type strain is one of the factors that makes the synthesis of the ultra high molecular weight PHA difficult.

A large number of studies on production of P(3HB-co-4HB) has been conducted. To *Cupriavidus necator*, which is a P(3HB)-producing wild-type strain, a carbon source, such as 4-hydroxybutyrate (4HB), γ-butyrolactone, 1,4-butanediol, 1,6-hexanediol, 1,8-octanediol, 1,10-decanediol and 1,12-dodecanediol, is fed, and after culturing, (3HB-co-4HB) can be produced.

A method for producing P(3HB-co-4HB) and/or P(4HB) using *E. coli*, which is not a P(3HB)-producing wild-type strain, after genetic modification has been reported. Initially, each of the genes, phaA, phaB, and phaC, respectively of β-ketothiolase (PhaA), acetoacetyl-CoA reductase (PhaB), and PHA synthase (PhaC), which are derived from *Cupriavidus necator*, that is necessary to produce P(3HB) from acetyl CoA, and additionally genes from succinate degradation pathway in *Clostridium kluyveri* (sueD, 4hbD, orfZ) were introduced to supply 4HB-CoA from succinic acid so as to produce P(3HB-co-4HB) having a molecular weight Mw of approximately 1800000 in *E. coli* on glucose as a carbon source; however, the 4HB proportion in the PHA was from 1.3 to 1.5%, which was low. (Non-Patent Document 4)

Furthermore, use of ε-caprolactone or 6-hydroxyhexanoate (or its salt), which is a saponified product of ε-caprolactone, to produce P(3HB-co-4HB) was also reported. In the case where *Cupriavidus necator* was cultured using ε-caprolactone as a carbon source, accumulation of P(3HB-co-4HB) along with the PHA content from 26 to 38% and the 4HB proportion from 30% to 36% was reported (Non-Patent Document 5); however, no molecular weights were mentioned.

Furthermore, although a genetically modified bacterium in which a PHA synthase gene of the genus *Aeromonas* is introduced to a PHA degrading enzyme deleted strain of *Cupriavidus necator* can produce in flask culture ultra high molecular weight P(3HB-co-3HH) having a weight average molecular weight Mw of 3000000 or greater, however, Mw merely reached approximately 2000000 in jar fermenter culture (Patent Document 1).

Furthermore, it is known that the molecular weight of a copolymer of lactic acid and 3HB increased by culturing a genetically modified bacterium in a medium to which a good solvent of polylactic acid such as dimethylsulfoxide (DMSO) was added (Patent Document 2).

Furthermore, Patent Document 3 describes a microorganism for synthesizing a PHA having a molecular weight and a method for producing a high molecular weight PHA by controlling a specific activity of a PHA synthase in a cell of a microorganism of the genus *Cupriavidus* that can produce a PHA, to 0.1 U/mg-protein or less. It is described that using the microorganism and the method of Patent Document 3 enables to industrially produce PHAs having weight average molecular weight of 4000000 or greater efficiently. Patent Document 4 describes production of a free hydroxy group-containing PHA by culturing a particular microorganism using δ-valerolactone and/or ε-caprolactone or culturing it using glycolic acid. Patent Documents 3 and 4 do not have descriptions as to controlling an osmotic pressure and a nitrogen atom concentration in a culture solution during culture. Furthermore, Patent Document 5 describes a β-hydroxybutyrate copolymer comprising from 50 to 99 mol % of β-hydroxybutyrate repeating units and from 1 to 50 mol % of β-hydroxyvalerate repeating units and having a weight average molecular weight of 50000 or greater. Patent Document 5 does not have descriptions as to controlling an osmotic pressure in a culture solution during culture.

PRIOR ART DOCUMENTS

Patent Documents

Patent Document 1: WO 2014/065253
Patent Document 2: JP 2017-29082 A
Patent Document 3: WO 2012/102371

Patent Document 4: WO 2017/033652
Patent Document 5: JP 5-15383 A

Non Patent Documents

Non-Patent Document 1: Alistair J. Anderson et al., Microbiological Reviews, Vol. 54, No. 4, 450-472, 1990

Non-Patent Document 2: Editors: M. Fontanille, A. Guyot, Recent Advances in Mechanistic and Synthetic Aspects of Polymerization. Book. NATO ASI Series, Vol. 215, 293-314, 1987

Non-Patent Document 3: S. Kusaka et al., Applied Microbiology and Biotechnology, Vol. 47, 140-143, 1997

Non-Patent Document 4: Henry E. Valentin et al., Journal of Biotechnology Vol. 58, 33-38, 1997

Non-Patent Document 5: Sung Chul Yoon et al., Korean Journal of Applied Microbiology and Biotechnology, Vol. 28, No. 2, 71-79, 2000

SUMMARY OF INVENTION

Problem to be Solved by the Invention

Physical properties of PHAs are expected to be improved through copolymerization and molecular weight increase of PHAs. P(3HB) has hard and brittle physical properties, and improvement of the physical properties is expected unlikely because the 3-hydroxyvalerate (3HV) unit undergoes cocrystallization even when subjected to copolymerization. However, for a copolymer PHA comprising a second component unit that does not undergo cocrystallization with a 3HB unit, such as a 4HB unit and a 3-hydroxyhexanoate (3HH) unit, significant improvement of physical properties is expected by changing the proportion of the second unit component. In particular, it is known that, P(3HB-co-4HB), in which 4HB units having no side chains compared to 3HB units are copolymerized, undergoes enzymatic degradation by lipases as well as PHA degrading enzyme while a PHA comprising 3HB units having side chains or other 3-hydroxyalkanoic acids does not show degradability by lipases, and the P(3HB-co-4HB) is expected to enhance degradability in a living system and its use as a medical material is expected. However, among production methods that use PHA-producing wild-type strains using 1,4-butanediol, γ-butyrolactone, or 4HB, which have been commonly used as 4HB unit precursors, a method for obtaining a P(3HB-co-4HB) copolymer having a weight average molecular weight Mw of greater than 1710000 is not known.

Since a PHA-producing wild-type strain degrades and uses an accumulated PHA as needed and has a PHA degrading enzyme in its cell, synthesis of an ultra high molecular weight PHA is said to be difficult, and gradual decrease in a molecular weight of PHA during a culture period is understood as a typical phenomenon.

In the case where a PHA is used as a medical material, high purifying technologies, such as endotoxin removal, are employed. Typically, PHA tends to degrade and the molecular weight tends to decrease, as the high purification is performed. Furthermore, in the case where the molecular weight of the PHA after the purification or productization needs to be a high molecular weight, the PHA is required to have an adequately high molecular weight in the stage of culture before purification because the molecular weight decreases by application of heat treatment, such as heating and melting. Even for products for general industries and not as medical materials, purification of a certain degree is necessary, and even higher molecular weights have been demanded for enhancement of physical properties of PHAs after purification. Therefore, a method that can provide a high molecular weight PHA compared to known technologies during culture has been demanded.

An object of the present invention is to provide a method for producing a polyester comprising at least a 3-hydroxybutyrate unit as a polymerization unit, and having a high molecular weight and a narrow molecular weight distribution (that is, small Mw/Mn).

Means for Solving the Problem

As a diligent research to solve the problems described above, the inventors of the present invention found that in culturing a microorganism having a polyester-producing capability to produce a polyester, maintaining an osmotic pressure of the culture solution from 200 mOsm to 900 mOsm and a nitrogen atom concentration of the culture solution at 0.30 g/L or greater enables to produce a polyester comprising at least a 3-hydroxybutyrate unit as a polymerization unit and having a weight average molecular weight of 1,000,000 or greater and a narrow molecular weight distribution. The present invention was completed based on the findings described above.

That is, according to the present invention, the following inventions are provided:

(1) A method for producing a polyester comprising culturing a microorganism having a polyester-producing capability in a culture solution containing a carbon source and a nitrogen source, the polyester comprising at least a 3-hydroxybutyrate unit as a polymerization unit, wherein the produced polyester has a weight average molecular weight of 1000000 or greater determined by gel permeation chromatography calibrated with polystyrene standards, and comprises at least the 3-hydroxybutyrate unit as the polymerization unit, and where the culture solution has a pH of 4 to 7.5, and the culture satisfies conditions (a) and (b) below:

(a) an osmotic pressure of the culture solution is maintained from 200 mOsm to 900 mOsm during culture period; and (b) a nitrogen atom concentration of the culture solution is maintained at 0.30 g/L or greater during culture period.

(2) The method according to (1), wherein the microorganism is selected from a group consisting of genera of Cupriavidus, Alcaligenes, Ralstonia, Delftia, Comamonas, Hydrogenophaga, Burkholderia, Escherichia, Azotobacter, Methylobacterium, Paracoccus, Acinetobacter, Aeromonas, Allochromatium, Azorhizobium, Bacillus, Caulobacter, Chromobacterium, Ectothiorhodospira, Klebsiella, Nocardia, Rhodobacter, Rhodococcus, Rhodospirillum, Rickettsia, Sinorhizobium, Sphingomonas, Synechocystis, Thiococcus, Thiocystis, Vibrio, and Wautersia.

(3) The method according to (1) or (2), wherein the microorganism is Cupriavidus necator.

(4) The method according to any one of (1) to (3), wherein a culture temperature is from 15° C. to 45° C.

(5) The method according to any one of (1) to (4), wherein the culture is a fed-batch culture or a continuous culture.

(6) The method according to any one of (1) to (5), wherein the carbon source contains at least one selected from a group consisting of ε-caprolactone, δ-valerolactone, δ-caprolactone, saponified products of ε-caprolactone, δ-valerolactone, and δ-caprolactone, and salts of the saponified product.

(7) A method for producing a polyester comprising culturing a microorganism having a polyester-producing capability in a culture solution containing a carbon source and a nitrogen source, the polyester comprising at least a 3-hydroxybutyrate unit as a polymerization unit, where
the produced polyester has a weight average molecular weight of 1000000 or greater determined by gel permeation chromatography calibrated with polystyrene standards, and comprises at least the 3-hydroxybutyrate unit as the polymerization unit, and wherein
the culture solution has a pH of 4 to 7.5,
the culture is a batch culture, and
the culture satisfies conditions (a) and (b) below:
(a) an osmotic pressure of the culture solution at the initiation of the culture is from 200 mOsm to 900 mOsm; and
(b) a nitrogen atom concentration of the culture solution at the initiation of the culture is 0.30 g/L or greater.

Advantageous Effects of Invention

According to the present invention, a polyester comprising at least a 3-hydroxybutyrate unit as a polymerization unit and having a molecular weight of 1000000 or greater and a narrow molecular weight distribution (that is, small Mw/Mn) can be produced.

EMBODIMENTS FOR CARRYING OUT THE INVENTION

Figure 1:
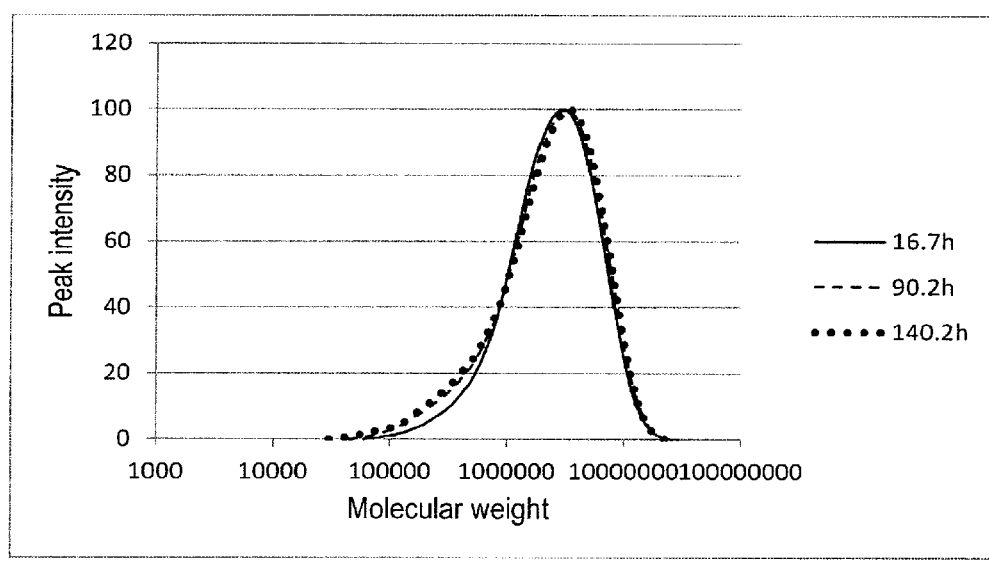
FIG. 1 illustrates a molecular weight distribution of PHA produced in Example 1.

Embodiments according to the present invention are described below.
[Method for Producing Polyester]
The polyester produced in the present invention is a polyester having a weight average molecular weight of 1,000,000 or greater determined by gel permeation chromatography calibrated with polystyrene standards and comprising at least a 3-hydroxybutyrate unit as a polymerization unit.
As described above, one of the characteristics of the present invention is that the produced polyester has a high molecular weight, which is the weight average molecular weight (Mw) of 1,000,000 or greater determined by gel permeation chromatography calibrated with polystyrene standards. The weight average molecular weight determined by gel permeation chromatography calibrated with polystyrene standards, is preferably 1,250,000 or greater, more preferably 1,380,000 or greater, even more preferably 1,800,000 or greater, and particularly preferably 1,900,000 or greater. The weight average molecular weight determined by gel permeation chromatography calibrated with polystyrene standards, may be 2,000,000 or greater, 2,100,000 or greater, 2,200,000 or greater, 2,300,000 or greater, 2,400,000 or greater, 2,500,000 or greater, 2,600,000 or greater, 2,700,000 or greater, 2,800,000 or greater, 2,900,000 or greater, 3,000,000 or greater, 3,100,000 or greater, 3,200,000 or greater, 3,300,000 or greater, 3,400,000 or greater, 3,500,000 or greater, 3,600,000 or greater, 3,700,000 or greater, 3,800,000 or greater, 3,900,000 or greater, or 4,000,000 or greater. The upper limit of the weight average molecular weight determined by gel permeation chromatography calibrated with polystyrene standards, is not particularly limited and is typically 20,000,000 or less, 10,000,000 or less, 8,000,000 or less, 7,000,000 or less, 6,000,000 or less, or 5,000,000 or less.

For the polyester, the number average molecular weight (Mn) is preferably 300,000 or greater determined by gel permeation chromatography calibrated with polystyrene standards. The number average molecular weight determined by gel permeation chromatography calibrated with polystyrene standards, may be 350,000 or greater, 400,000 or greater, 450,000 or greater, 500,000 or greater, 550,000 or greater, 600,000 or greater, 650,000 or greater, 700,000 or greater, 750,000 or greater, 800,000 or greater, 850,000 or greater, 900,000 or greater, 950,000 or greater, 1,000,000 or greater, 1,100,000 or greater, 1,200,000 or greater, or 1,300,000 or greater. The upper limit of the number average molecular weight determined by gel permeation chromatography calibrated with polystyrene standards, is not particularly limited and is typically 10,000,000 or less, and may be 5,000,000 or less, 4,000,000 or less, 3,000,000 or less, or 2,000,000 or less.

The ratio of Mw to Mn (Mw/Mn) is not particularly limited and is, for example, from 1.0 to 10.0, from 1.0 to 6.0, or from 1.0 to 4.0, and an even smaller value is preferred. The ratio of Mw to Mn (Mw/Mn) is preferably from 1.0 to 3.3, more preferably from 1.0 to 3.0, and even more preferably from 1.0 to 2.9, and may be from 1.0 to 2.5.

In the present invention, even with a PHA-producing wild-type strain having a PHA degrading enzyme, a PHA having a high molecular weight and a narrow molecular weight distribution can be produced without causing significant reduction in molecular weight in a later stage of the culture.

The measurement of the weight average molecular weight by gel permeation chromatography calibrated with polystyrene standards, can be performed by the same method described as that described in Examples below.

The polyester produced in the present invention at least contains a 3-hydroxybutyrate unit as a polymerization unit. That is, the polyester may be one comprising only a 3-hydroxybutyrate unit as a polymerization unit or may be the one comprising a 3-hydroxybutyrate unit and other polymerization unit as polymerization units. Examples of the other polymerization unit besides the 3-hydroxybutyrate unit include a 4-hydroxybutyrate unit, and further include the polymerization units derived from lactate (LA), glycolate (GA), 3-hydroxypropionate (3HP), 3-hydroxyvalerate (3HV), 5-hydroxyvalerate (5HV), 5-hydroxyhexanoate (5HH), 6-hydroxyhexanoate (6HH), 3-hydroxyhexanoate (3HH), and hydroxyalkanoate having 7 or more carbons.

The polyester comprising a 4-hydroxybutyrate unit besides the 3-hydroxybutyrate unit may be a polyester comprising only the 3-hydroxybutyrate unit and the 4-hydroxybutyrate unit as the polymerization units (that is, the polymerization units consist of the 3-hydroxybutyrate unit and the 4-hydroxybutyrate unit) or may be a polyester comprising a 3-hydroxybutyrate unit and a 4-hydroxybutyrate unit as polymerization units and further comprising other polymerization unit besides those described above. Examples of such another polymerization unit include lactate (LA), glycolate (GA), 3-hydroxypropionate (3HP), 3-hydroxyvalerate (3HV), 5-hydroxyvalerate (5HV), 5-hydroxyhexanoate (5HH), 6-hydroxyhexanoate (6HH), 3-hydroxyhexanoate (3HH), and hydroxyalkanoate having 7 or more carbons.

In the present invention, the 3-hydroxybutyrate unit and the 4-hydroxybutyrate unit are represented by the following formulas.

3-Hydroxybutyrate unit: —OCH(CH$_3$)CH$_2$C(=O)—
4-Hydroxybutyrate unit: —OCH$_2$CH$_2$CH$_2$C(=O)—

In the case where the polyester contains a 3-hydroxybutyrate unit and a 4-hydroxybutyrate unit, the proportion of the 4-hydroxybutyrate unit relative to all monomer units is not particularly limited and is preferably from 3 mol % to 40 mol %, more preferably from 10 mol % to 40 mol %, and even more preferably from 14 mol % to 40 mol %. The proportion of the 4-hydroxybutyrate unit relative to all monomer units may be 15 mol % or greater, 16 mol % or greater, 17 mol % or greater, 18 mol % or greater, 19 mol % or greater, or 20 mol % or greater. The proportion of the 4-hydroxybutyrate unit relative to all monomer units may be 20.2 mol % or greater, 20.6 mol % or greater, 21 mol % or greater, 22 mol % or greater, 23 mol % or greater, 24 mol % or greater, 25 mol % or greater, 26 mol % or greater, 27 mol % or greater, or 28 mol % or greater. The proportion of the 4-hydroxybutyrate unit relative to all monomer units may be 35 mol % or less, 34 mol % or less, 33 mol % or less, 32 mol % or less, 31 mol % or less, 30 mol % or less, 29 mol % or less, 28 mol % or less, 27 mol % or less, 27 mol % or less, 26 mol % or less, or 25 mol % or less.

The proportion of the 4-hydroxybutyrate unit relative to all monomer units can be measured in accordance with the method described in Examples below.

The polyester may be any one selected from a random polymer, a block polymer, an alternating polymer, and a grafted polymer, but is preferably a random polymer.

As the microorganisms having a P(3HB)-producing capability, microorganisms of the genera of *Cupriavidus, Alcaligenes, Ralstonia, Delftia, Comamonas, Hydrogenophaga, Burkholderia, Escherichia, Azotobacter, Methylobacterium, Paracoccos, Pseudomonas, Acinetobacter, Aeromonas, Allochromatium, Azorhizobium, Bacillus, Caulobacter, Chromobacterium, Ectothiorhodospira, Klebsiella, Nocardia, Rhodobacter, Rhodococcus, Rhodospirillum, Rickettsia, Sinorhizobium, Sphingomonas, Synechocystis, Thiococcus, Thiocystis, Vibrio*, and *Wautersia* can be used. Among these, genus *Cupriavidus* is preferred, and *Cupriavidus necator* is more preferred. For example, *Cupriavidus necator* H16 (ATCC17699) can be used.

Note that, with the *Cupriavidus necator* H16 wild-type strain, 3HB, 3HV, 4HB, 5HV or the like can be adequately incorporated into PHA; however, use of genetically modified bacteria, in which a PHA synthase gene having a different substrate specificity has been introduced, enables polymerization of another hydroxy acid into the PHA. Thus, as described above, in addition to a *Cupriavidus necator* H16 wild-type strain, genetically modified microorganisms having a PHA-polymerizing capability also can be used, which include other *Cupriavidus* species, as well as the genera of *Alcaligenes, Ralstonia, Delftia, Comamonas, Hydrogenophaga, Burkholderia, Escherichia, Azotobacter, Methylobacterium, Paracoccos, Pseudomonas, Acinetobacter, Aeromonas, Allochromatium, Azorhizobium, Bacillus, Caulobacter, Chromobacterium, Ectothiorhodospira, Klebsiella, Nocardia, Rhodobacter, Rhodococcus, Rhodospirillum, Rickettsia, Sinorhizobium, Sphingomonas, Synechocystis, Thiococcus, Thiocystis, Vibrio*, and *Wautersia*.

In the present invention, the microorganisms having a P(3HB)-producing capability is cultured in a culture solution containing a carbon source and a nitrogen source.

A pH of the culture solution is from 4 to 7.5. The pH may be less than 7.0, 6.5 or less, 6.4 or less, 6.3 or less, or 6.1 or less, and may be 4.5 or greater, 5.0 or greater, 5.1 or greater, 5.2 or greater, 5.3 or greater, 5.4 or greater, or 5.5 or greater.

The culture temperature is typically from 15° C. to 45° C., preferably from 20° C. to 40° C., and more preferably from 25° C. to 38° C.

The culture method may be any one of batch culture, fed-batch culture, or continuous culture.

In the present invention, the culture conditions satisfy the following conditions (a) and (b):

(a) an osmotic pressure of the culture solution is maintained from 200 mOsm to 900 mOsm during culture period; and (b) a nitrogen atom concentration of the culture solution is maintained at 0.30 g/L or greater during the culture period.

It was found that a polyester having a high molecular weight and a narrow molecular weight distribution (that is, small Mw/Mn) can be produced by employing the culture conditions satisfying the conditions (a) and (b).

The description "maintained" in "(a) an osmotic pressure of the culture solution is maintained from 200 mOsm to 900 mOsm during culture period" and "(b) a nitrogen atom concentration of the culture solution is maintained at 0.30 g/L or greater during the culture period" means that the osmotic pressure of the culture solution and the nitrogen atom concentration of the culture solution need only to satisfy the conditions described above in the most of the culture period (e.g., 95% or greater, 96% or greater, 97% or greater, 98% or greater, or 99% or greater) and do not require the osmotic pressure of the culture solution and the nitrogen atom concentration of the culture solution to satisfy the conditions described above at all times over the entire culture period (that is, 100% of the culture period). For example, the osmotic pressure of the culture solution and/or the nitrogen atom concentration of the culture solution may be out of the range of the condition described above for a short period of time in the culture period (e.g., 6 hours or less, 5 hours or less, 4 hours or less, 3 hours or less, 2 hours or less, 1 hour or less, 30 minutes or less, 20 minutes or less, 10 minutes or less, or 5 minutes or less). Also, the state where the osmotic pressure of the culture solution and/or the nitrogen atom concentration of the culture solution is out of the range of the condition described above may occur for a plurality of times during one culture process as long as the effect of the present invention is not impaired.

The osmotic pressure of the culture solution in the culture period is preferably from 200 mOsm to 900 mOsm, more preferably from 200 mOsm to 800 mOsm, even more preferably from 200 mOsm to 700 mOsm, yet even more preferably from 200 mOsm to 600 mOsm, and particularly preferably from 200 mOsm to 500 mOsm. The lower limit of the osmotic pressure need only to be 200 mOsm or greater, and may be 210 mOsm or greater, 220 mOsm or greater, 230 mOsm or greater, 240 mOsm or greater, 250 mOsm or greater, or 300 mOsm or greater. The upper limit of the osmotic pressure need only be 900 mOsm or less, and may be 800 mOsm or less, 700 mOsm or less, 600 mOsm or less, 500 mOsm or less, or 400 mOsm or less.

The nitrogen atom concentration of the culture solution in the culture period is 0.30 g/L or greater, and preferably 0.40 g/L or greater, 0.42 g/L or greater, 0.50 g/L or greater, 0.55 g/L or greater, 0.63 g/L or greater, or 0.78 g/L or greater. The upper limit of the nitrogen atom concentration is not particularly limited and is typically 15.6 g/L or less, or 7.8 g/L or less.

The $NH_4^+$ concentration in the culture solution in the culture period is preferably 0.39 g/L or greater, and may be 0.40 g/L or greater, 0.51 g/L or greater, 0.54 g/L or greater, 0.64 g/L or greater, 0.70 g/L or greater, 0.81 g/L or greater, or 1.00 g/L or greater. The upper limit of the $NH_4^+$ concentration is not particularly limited and is typically 20.0 g/L or less, or 10.0 g/L or less.

As described below in the present specification, in the present invention, it was found that the simultaneous satisfaction of the condition (a) for the osmotic pressure and the condition (b) for the nitrogen atom concentration allow PHA accumulation in a non-growth-associated manner, and thus a high molecular weight PHA can be accumulated. It was first discovered by the present invention that a high molecular weight PHA can be accumulated by controlling the osmotic pressure and the nitrogen atom concentration.

The measurement method of the osmotic pressure is not particularly limited and can be measured by the freezing-point depression method described in Examples below.

The measurement method of the nitrogen atom concentration of the culture solution is not particularly limited, either. The nitrogen atom concentration can be determined by quantitative determination of ammonium ion described in Examples below and converting the ammonium ion concentration into the nitrogen atom concentration based on the following equation.

Ammonium ion concentration (g/L)×14/18=nitrogen atom concentration (g/L)

The medium component is not particularly limited as long as it is a substance that can be assimilated by the microorganisms to be used, and is preferably a substance other than substances contributing to chain transfer of the PHA polymerization.

As the carbon source, for example, organic carbon sources, such as methanol, ethanol, butanol, acetic acid, and butyric acid; inorganic carbon sources, such as carbon dioxide; natural materials, such as yeast extract, molasses, peptone, and meat extract; saccharides, such as arabinose, glucose, mannose, fructose, and galactose; sorbitol, mannitol, and inositol can be used. Note that, since short-chain alcohols, such as methanol, ethanol, or butanol, may act as chain transfer agents, the carbon source is preferably a carbon source other than methanol, ethanol, and butanol.

As the nitrogen source, for example, inorganic nitrogen compounds, such as ammonia, ammonium salts (ammonium chloride, ammonium sulfate, ammonium phosphate), and nitrate; and/or organic nitrogen-containing substances, such as urea, corn steep liquor, casein, peptone, yeast extract, and meat extract can be used.

In the batch culture, it is acceptable as long as the transition to non-growth-associated PHA production due to the occurrence of the depletion of the nitrogen source prior to the depletion of the carbon source is avoided, and for example, in the flask culture condition, greater than or equal to 2 g/L of ammonium sulfate is preferably added. Furthermore, in the fed-batch culture or the continuous culture, it is desirable to maintain the nitrogen atom concentration of 0.30 g/L or greater (or 0.42 g/L or greater or 0.55 g/L or greater) or the osmotic pressure of 200 mOsm or greater.

Furthermore, in the batch culture, the osmotic pressure at the initiation of the culture only needs to be 200 mOsm or greater although the osmotic pressure before the culture increases due to addition of salts, such as ammonium sulfate and sodium chloride, as well as the carbon source, and the osmotic pressure may be reduced to less than 200 mOsm at the end of the culture due to consumption of the carbon source and other mineral components.

Examples of the inorganic component include calcium salts, magnesium salts, potassium salts, sodium salts, phosphate, manganese salts, zinc salts, iron salts, copper salts, molybdenum salts, cobalt salts, nickel salts, chromium salts, boron compounds, and iodine compounds. More specific examples thereof include monopotassium phosphate, dipotassium phosphate, magnesium phosphate, magnesium sulfate, and sodium chloride.

Examples of other organic nutrient source include amino acids, such as glycine, alanine, serine, threonine, and proline; and vitamins, such as vitamin B1, vitamin B 12, and vitamin C.

According to a preferred embodiment of the present invention, the carbon source contains at least one selected from a group consisting of ε-caprolactone, δ-valerolactone, δ-caprolactone, saponified products of ε-caprolactone, δ-valerolactone and δ-caprolactone, and salts of ε-caprolactone, δ-valerolactone and δ-caprolactone. As the carbon source, at least one selected from a sugar, a fat, a fatty acid, an amino acid and a peptide may further be included.

In the present invention, use of a water-soluble component that contributes to increase of the osmotic pressure and is less likely to be a chain transfer agent described below is preferred to maintain the osmotic pressure. Examples of such a component include inorganic salts such as NaCl; nitrogen-containing inorganic salts such as $(NH_4)_2SO_4$; carbon sources such as saccharides or short chain fatty acids; organic solvent carbon sources that can be assimilated such as ε-caprolactone; and organic solvents such as DMSO.

When ε-caprolactone is added to the culture, ε-caprolactone is subjected to ring opening to form 6-hydroxyhexanoate (6HH), then CoA is added thereto to form 6HH-CoA. The acetyl CoA is removed by a β-oxidation system, and 4HB-CoA remains and is incorporated into the PHA to become a 4HB unit. 6HH-CoA is less likely to be incorporated into the PHA because of the substrate specificity of the PHA synthase, and P(3HB-co-4HB) is accumulated.

4HB-CoA also produces acetyl CoA when being subjected to β-oxidation.

A reaction, in which a hydroxy group-containing compound is incorporated into an enzyme-S-PHA complex of the PHA synthase during elongation and break off a thioester between the enzyme and the PHA polymer chain, and then the PHA polymer chain transfers from the enzyme to a chain transfer agent to terminate the PHA polymerization, is called a chain transfer reaction in radical polymerization. There is a possibility that since 4HB and diols are hydroxy group-containing compounds, and γ-butyrolactone also undergoes ring-opening to form 4HB, these hydroxy group-containing compounds may act as chain transfer agents during the PHA polymerization and may stop the polymerization of the PHA. In particular, since one or both of the two hydroxy groups at the terminals of diols can involve in the chain transfer, it is believed that the diols in particular tend to terminate the PHA polymerization, making a high molecular weight PHA unlikely to be obtained.

When ε-caprolactone is subjected to ring opening to form 6HH, which is a hydroxy group-containing compound. 4HB-CoA is likely a substrate for the PHA synthase, but 6HH-CoA is less likely to be a substrate. Similarly, it is conceived that 6HH is less likely to act as a chain transfer agent compared to 4HB, and thus a higher molecular weight PHA can be obtained when ε-caprolactone is used. For the same reason, it is conceived that a high molecular weight PHA can be obtained in the case of using δ-valerolactone or δ-caprolactone although composition and compositional ratio of PHA are different.

Substance production by microorganisms include growth-associated production and non-growth-associated production.

In the growth-associated PHA production, PHA is accumulated while the bacterial cell component other than the PHA proliferates. In the growth-associated PHA production, acetyl CoA is used by both the PHA synthesis and the bacterial cell proliferation, and the acetyl CoA is less likely to be surplus. It is presumed that, during the growth-associated PHA production, generation of free hydroxy acid due to degradation of the PHA is suppressed, and thus chain transfer reaction is less likely to occur and the molecular weight becomes relatively high.

In the non-growth-associated PHA production, the PHA accumulation occurs and increases the PHA content after the proliferation of the bacterial cell component has been stopped. Since the bacterial cell proliferation has stopped, surplus acetyl CoA is used for the PHA production. During the non-growth-associated PHA production, it seems that the component temporarily taken into the form of PHA undergoes re-differentiation, and free hydroxy acid is discharged out of the bacterial cell. It is presumed that, in the case where the nitrogen source is depleted in the later stage of the culture, transition from the growth-associated production to the non-growth-associated production occurs, chain transfer reactions frequently occur, and the synthesis and the degradation tend to occur at the same time (conditions where the molecular weight easily decreases).

In the present invention, it was found that, in the case where the PHA is accumulated in a growth-associated manner, a high molecular weight PHA is predominantly accumulated compared to the case where the PHA is accumulated in a non-growth-associated manner under nutrient limitation. That is, in the production of polyester according to the present invention, as opposed to the non-growth-associated PHA production due to limited nutrients, where proliferation of the bacterial cells and accumulation of the PHA are separated, the growth-associated PHA production, where proliferation of the bacterial cells and accumulation of the PHA occur simultaneously, is preferred.

Note that, in the present invention, it was found that the PHA production associated with proliferation is observed in the case where *Cupriavidus necator* is cultured while sufficient nitrogen source is present and a certain degree of osmotic pressure is ensured. It has been known that, in the production of P(3HB) or P(3HB-co-4HB) using *Cupriavidus necator* H16 (ATCC17699), the molecular weight of the PHA decreases in the case where a chain transfer agent (e.g., polyethylene glycol (PEG)) is added to a medium. Binding of PEG to the carboxy terminus of PHA for P(3HB-co-4HB) production using 4HB as a carbon source has been observed in non-growth-associated PHA production by employing, for example, nitrogen limitation (Macromolecules (1996), 29 (1), 10-17). However, no data showing the binding between P(3HB) and PEG for P(3HB) production using fructose as a carbon source was obtained, and there was an opinion that the molecular weight of the P(3HB) was reduced, because the PEG and the PHA synthase interacted and the frequency of termination of PHA polymerization was increased due to chain transfer caused by water, rather than PEG (Macromolecules (1996), 29 (24), 7753-7758).

Figure 8:
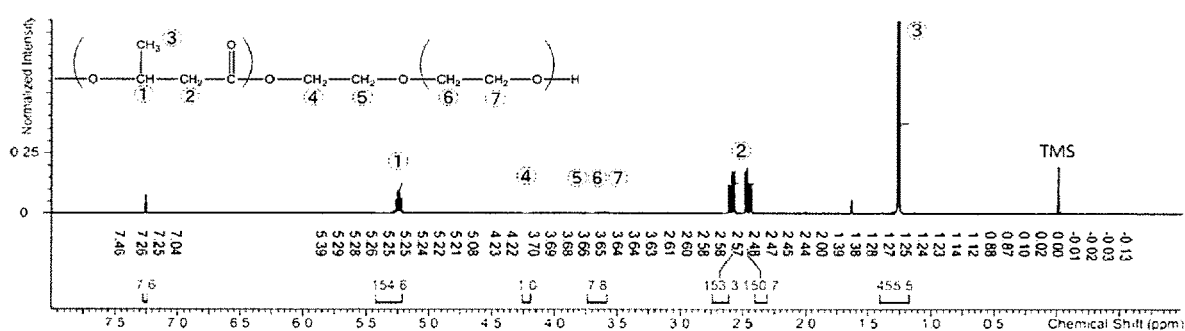
FIG. 8 shows $^1$H-NMR of PEGylated P(3HB) extracted and purified from a culture solution obtained in Comparative Example 17 on the third day of culture.
Figure 9:
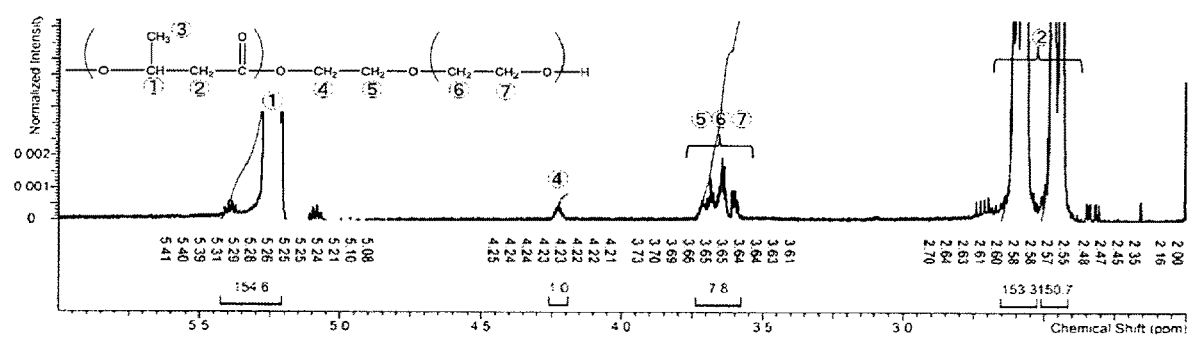
FIG. 9 shows a magnified view of FIG. 8.
Figure 10:
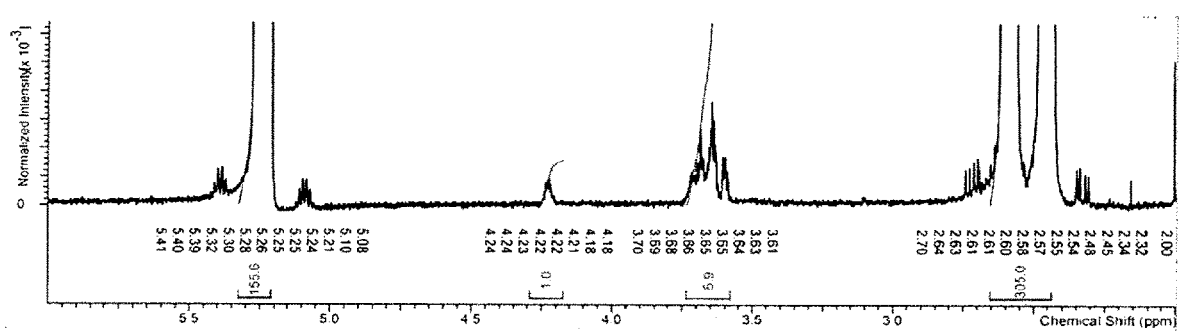
FIG. 10 shows a magnified view of $^1$H-NMR of PEGylated P(3HB) extracted and purified from a culture solution of Comparative Example 17 on the fifth five day of culture.

In the present invention, in the case where the growth-associated P(3HB) production was performed using *Cupriavidus necator* H16 in the presence of PEG, direct binding between the P(3HB) and the PEG was confirmed by NMR analysis (Comparative Example 17, Table 26, and FIG. 8 to FIG. 10 of the present specification). It is presumed that, even when the chain transfer by the PEG occurred in the non-growth-associated P(3HB) production, a terminal ester bond between the P(3HB) and the PEG was rapidly broken due to the effect of the PHA degrading enzyme in the bacterial cells, and thus it was only observed that the PEG molecule did not bind to the terminus of P(3HB). However, it is conceived that, under a condition for the growth-associated P(3HB) production where a high molecular weight polymer could be obtained without addition of chain transfer agent, PHA degradation might be suppressed, the molecular weight reduction was observed due to the addition of PEG as a chain transfer agent, and additionally, the fact that the binding between the P(3HB) and the PEG was not broken down, but remained could be directly observed by $^1$H-NMR.

The culture time in the method of the present invention is not particularly limited and is typically 24 hours or longer, 48 hours or longer, 72 hours or longer, 96 hours or longer, or 120 hours or longer. The upper limit of the culture time is not particularly limited and is typically 240 hours or less, 216 hours or less, or 192 hours or less.

From the culture solution obtained by culturing in accordance with the method of the present invention, dried bacterial cells can be obtained by separating and collecting the bacterial cells by a typical solid-liquid separation means, such as filtration and centrifugal separation, then washing and drying the bacterial cells. The polyester can be collected by a common method, for example, comprising extracting a produced polyester from the dried bacterial cells with an organic solvent such as chloroform, and adding a poor solvent such as hexane into this extracted liquid to precipitate the polyester, and collecting the polyester.

The present invention will be described more specifically hereinafter using examples, but the present invention is not limited to the following examples.

EXAMPLES

[Production of Copolymer Polyester by *Cupriavidus Necator* H16]

Example 1

PHA was produced by using *Cupriavidus necator* H16 (ATCC17699).

A medium obtained by adding 14.24 g/L of fructose into a sterilized medium 1 containing 2.72 g/L of $KH_2PO_4$, 4.26 g/L of $Na_2HPO_4$, 0.3 g/L of $NaHCO_3$, 2 g/L of $(NH_4)_2SO_4$, 0.2 g/L of $MgSO_4 \cdot 7H_2O$, 0.2 g/L of a yeast extract, and 3.5 mL of a mineral solution was subjected to shaking culture in a test tube at 30° C. for 24 hours to obtain a pre-preculture solution.

Mineral solution: dissolved in water are 6 g/L of $FeC_6H_5O_7 \cdot xH_2O$, 2 g/L of $ZnSO_4 \cdot 7H_2O$, 0.1 g/L of $CuSO_4 \cdot 5H_2O$, 1 g/L of $MnCl_2 \cdot 4H_2O$, 0.1 g/L of KI, 0.1 g/L of $(NH_4)_6Mo_7O_{24} \cdot 4H_2O$, 0.1 g/L of $CoCl_2 \cdot 6H_2O$, 0.2 g/L of $H_3BO_3$, 5 g/L of NaCl, and 4 g/L of $CaCl_2 \cdot 2H_2O$.

In an Erlenmeyer flask having a volumetric capacity of 500 mL containing 100 mL of a medium obtained by adding 14.24 g/L of fructose to the aforementioned medium 1 or a medium obtained by adding 8.86 g/L of fructose and 5.38 g/L of ε-caprolactone to the medium 1, 1 mL of the preculture solution was inoculated and cultured at 30° C. and 150 rpm for 48 hours to 96 hours to obtain a mother culture (preculture solution).

In a 3 L jar fermenter, 2 L of a medium was prepared by changing the amount of $(NH_4)_2SO_4$ of the aforementioned medium 1 to be 12.5 g/L. After the medium was sterilized, 100 mL of the mother culture was inoculated into the medium, and then fed-batch process using a sugar solution obtained by dissolving 12.4 g/L of NaCl in a 42 mass % fructose solution, and ε-caprolactone was started aseptically through a sterilizing filter (PTFE 0.2 μm pore). Feed rate and feed ratio of the carbon source can be set appropriately. To prevent termination of the bacterial cell proliferation caused by excessive amount of residual carbon source that was not used up by the bacterial cells in the culture vessel, the culture was started at a feed rate of the sugar solution of approximately 1 to 2 g/h (0.5 to 1 g/h·L) and at a feed rate of ε-caprolactone of approximately 0.2 to 0.5 g/h (0.1 to 0.25 g/h·L) which were low flow rates, and these feed rates were increased stepwise or continuously as the bacterial cells proliferated. The ventilation volume was controlled to 0.2 to 0.3 L/min, the agitation speed was controlled to 500 to 700 rpm, the culture temperature was controlled to 36° C., and the lower limit of the culture pH was controlled to 6.0. 12.5% ammonia water was used as a pH-adjusting alkali. The weight ratio of the 4HB precursor carbon source (ε-caprolactone in Example 1) to fructose was approximately 0.5. The culture was terminated at 140.2 hours after the start of the culture.

During the culture or after the culture, the bacterial cells and the culture supernatant were collected by centrifugal separation, and the bacterial cells were frozen at −20° C. and then subjected to lyophilization.

The lyophilized bacterial cells were used for PHA composition analysis and PHA molecular weight analysis.

The PHA composition analysis was performed by analyzing, for example, methyl esters derived from monomer units constituting the PHA by gas chromatography after methyl esterification.

The molecular weight analysis of the PHA was performed by subjecting the PHA extracted from the lyophilized bacterial cells by using chloroform to a gel permeation chromatography method. The molecular weight distribution of the PHA in Example 1 is shown in FIG. 1.

The culture supernatant was used for the osmotic pressure measurement and the ammonia concentration measurement.

Example 2

The same procedure as in Example 1 was performed except for adding 2.5 g/L of NaCl in the medium in the jar culture, using a medium in which the amount of $(NH_4)_2SO_4$ was changed to 10 g/L, using a 42 mass % fructose solution and ε-caprolactone as carbon sources of the fed-batch, and changing the culture time to 140.2 hours.

Example 3

The same procedure as in Example 1 was performed except for using a 42 mass % fructose solution and ε-caprolactone as carbon sources of the jar culture, and changing the culture time to 100 hours.

Comparative Example 1

The same procedure as in Example 3 was performed except for using a medium in which the amount of $(NH_4)_2SO_4$ in the medium in the jar culture was changed to 7.5 g/L and changing the culture time to 122.5 hours.

Comparative Example 2

The same procedure as in Example 3 was performed except for using a medium in which the amount of $(NH_4)_2SO_4$ in the medium in the jar culture was changed to 4 g/L and changing the culture time to 125.5 hours.

Comparative Example 3

The same procedure as in Example 3 was performed except for using 4N NaOH as the pH-adjusting alkali in the jar culture, and changing the culture time to 173.3 hours.

Comparative Example 4

The same procedure as in Comparative Example 3 was performed except for changing the amount of $(NH_4)_2SO_4$ in the medium in the jar culture to 10 g/L and changing the culture time to 140.5 hours.

Comparative Example 5

The same procedure as in Comparative Example 3 was performed except for changing the amount of $(NH_4)_2SO_4$ in the medium in the jar culture to 7.5 g/L and changing the culture time to 165.5 hours.

Comparative Example 6

The same procedure as in Comparative Example 5 was performed except for changing the pH lower limit control to pH 6.5 in the jar culture, and changing the culture time to 122 hours.

Comparative Example 7

Figure 2:
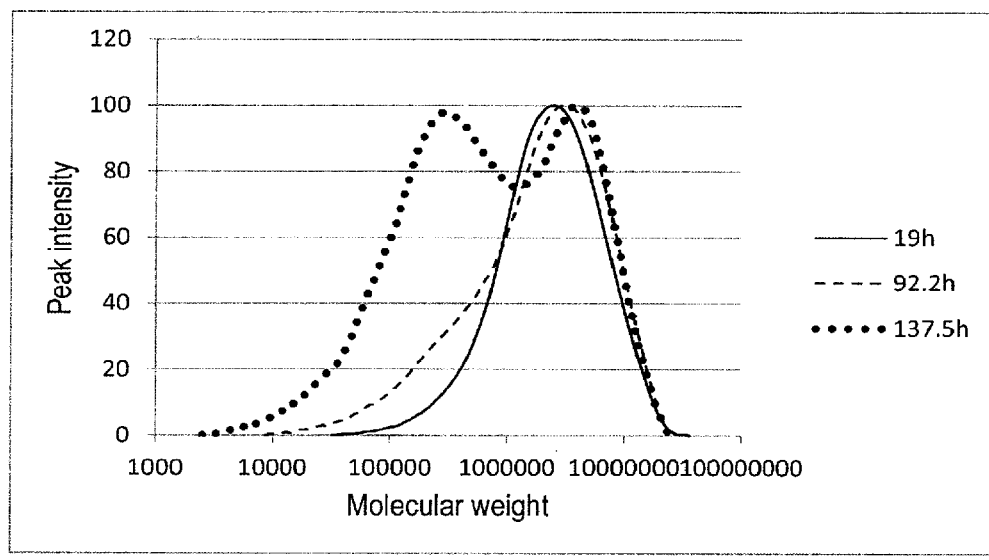
FIG. 2 shows a molecular weight distribution of PHA produced in Comparative Example 7.

The same procedure as in Comparative Example 5 was performed except for changing the pH lower limit control to pH 7 in the jar culture, and changing the culture time to 137.7 hours. The molecular weight distribution of the PHA in Comparative Example 7 is shown in FIG. 2.

Comparative Example 8

The same procedure as in Comparative Example 5 was performed except for changing the pH lower limit control to pH 7.5 in the jar culture, and changing the culture time to 149 hours.

Reference Example 1

The same procedure as in Example 3 was performed except for using a 42 mass % fructose solution and γ-butyrolactone as carbon sources of the preculture in the flask and the jar culture, and changing the culture time to 105 hours.

Reference Example 2

The same procedure as in Reference Example 1 was performed except for changing the weight ratio of the 4HB precursor (γ-butyrolactone in Reference Example 2) to fructose to be approximately 0.6.

Comparative Example 11

The same procedure as in Reference Example 1 was performed except for using a medium in which the amount of (NH$_4$)$_2$SO$_4$ in the medium in the jar culture was changed to 7.5 g/L, using 2N NaOH as the pH-adjusting alkali, and changing the culture time to 165 hours.

Comparative Example 12

The same procedure as in Example 3 was performed except for using a 42 mass % fructose solution and 1,4-butanediol as carbon sources of the preculture in the flask and the jar culture, changing the weight ratio of the 4HB precursor (1,4-butanediol in Comparative Example 12) to fructose to be approximately 0.7, and changing the culture time to 208.5 hours.

Comparative Example 13

The same procedure as in Comparative Example 12 was performed except for changing the weight ratio of the 4HB precursor (1,4-butanediol in Comparative Example 13) to fructose to be approximately 0.5.

Comparative Example 14

The same procedure as in Comparative Example 13 was performed except for using a medium in which the amount of (NH$_4$)$_2$SO$_4$ in the medium in the jar culture was changed to 7.5 g/L, using 2N NaOH as the pH-adjusting alkali, and changing the culture time to 189.5 hours.

Example 4

Figure 3:
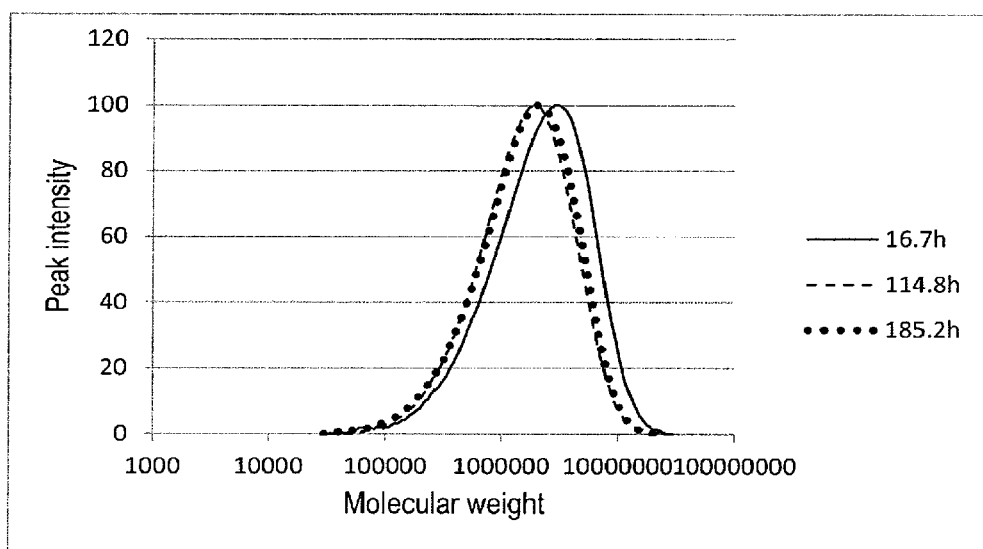
FIG. 3 shows a molecular weight distribution of PHA produced in Example 4.

The same procedure as in Example 1 was performed except for using a 42 mass % fructose solution as a carbon source of the preculture in the flask and the jar culture, and changing the culture time to 185.2 hours. The molecular weight distribution of the PHA in Example 4 is shown in FIG. 3.

Example 5

The same procedure as in Example 2 was performed except for using a 42 mass % fructose solution as a carbon source of the preculture in the flask and the jar culture, and changing the culture time to 185.9 hours.

Example 6

The same procedure as in Example 3 was performed except for using a 42 mass % fructose solution as a carbon source of the preculture in the flask and the jar culture, and changing the culture time to 150 hours.

The method of extracting and purifying the PHA from the bacterial cells was performed as described below. In a glass Erlenmeyer flask with a screw cap, approximately 4 to 10 g of the lyophilized bacterial cells were suspended in 400 mL chloroform and subjected to extraction at 30° C. for 24 to 48 hours. The obtained viscous solution was filtered by a filter paper to remove the bacterial cell residue. The obtained clear solution was concentrated to approximately 100 to 200 mL by an evaporator, and the PHA was precipitated by 5-fold amount of hexane, which was a poor solvent. The obtained white precipitates were washed with ethanol and then vacuum-dried to obtain purified PHA.

Comparative Example 15

The same procedure as in Comparative Example 2 was performed except for using a 42 mass % fructose solution as a carbon source of the preculture in the flask and the jar culture, and changing the culture time to 84 hours.

Comparative Example 16

The same procedure as in Comparative Example 5 was performed except for using a 42 mass % fructose solution as a carbon source of the preculture in the flask and the jar culture, using a medium in which the amount of (NH$_4$)$_2$SO$_4$ in the medium in the jar culture was changed to 4 g/L, and changing the culture time to 92.6 hours.

Comparative Example 17

(PEG 200 Added Culture: Production of PEGylated P(3HB)

The same procedure as in Example 1 was performed except for using a 42 mass % fructose solution as a carbon source of the preculture in the flask and the jar culture, adding 2.5 g/L of NaCl and 20 mL/L of PEG 200 in the medium in the jar culture, and changing the culture time to 130.9 hours. The culture solution after three days and the culture solution after five days of the culture were collected. The bacterial cells were collected by centrifugal separation, frozen at −20° C., and then subjected to lyophilization.

[Explanation of Analysis Method]

<PHA Molecular Weight Measurement (Gel Permeation Chromatography (GPC) Method)>

The PHA molecular weight measurement was performed by gel permeation chromatography method as described below.

The PHA derived from the lyophilized bacterial cells was adjusted to approximately 0.5 mg/mL by adding chloroform, extracted and dissolved at 60° C. for 4 hours, and cooled to room temperature. Insoluble substances were filtered and removed by using a PTFE filter having a pore diameter of 0.2 μm to obtain a measurement sample. Conditions for GPC are as shown below.

Instrument: HPLC Prominence system, available from Shimadzu Corporation

Column: Shodex K-806L (two columns in series), available from Showa Denko K.K.

Column temperature: 40° C.

Mobile phase: Chloroform (1 mL/min)

Detector: RI (40° C.)

Standards: Shodex polystyrene molecular weight standards (6870000 to 1270)

Injection amount: 60 μL

Analysis time: 30 minutes

<PHA Composition Analysis (GC Method)>

The composition analysis of the PHA contained in the bacterial cells was performed as described below. Approximately 10 mg of the obtained dried bacterial cells was weighed in a test tube with a screw cap, mixed with 2 mL of chloroform and 2 mL of an internal standard mixed solution of methanol and sulfuric acid (internal standard: benzoic acid 0.5 g/L; sulfuric acid 3.7 mass %), subjected to a heat treatment at 121° C. for 90 minutes, and then cooled to room temperature to subject the PHA to methyl esterification. After the termination of the reaction, 1 mL of pure water was added. Following vigorous agitation and centrifugal separation, an organic solvent layer was obtained. This organic solvent layer was dehydrated by sodium sulfate and then analyzed by gas chromatography to calculate the PHA component content. Conditions for GC are as shown below.

Gas Chromatography Analysis Conditions
Instrument: Shimadzu GC-2025
Capillary column: DB-1 (0.25 mm (id)×60 m; film thickness: 1 μm)
Carrier gas: He (3.23 mL/min)
Column temperature: 125° C. 6.5 min-rate 25° C./min −260° C.
Makeup flow rate: 30 mL/min
H2 flow rate: 40 mL/min
Air flow rate: 400 mL/min
Injection: 250° C.
Detector: FID (260° C.)
Split: 1:20
Injection amount: 1 μL
Analysis time: 21.5 min <Quantitative Determination Method of Ammonium Ion (CE Method)>

The quantitative determination of $NH_4^+$ concentration in the culture supernatant was performed as described below. The culture solution was subjected to centrifugal separation, and the obtained culture supernatant was used as is or after appropriate dilution. The $NH_4$ concentration of the culture supernatant was calculated by using 7100 Capillary Electrophoresis System, available from Agilent Technologies, Inc., with Multication Standard Solution III ($NH_4^+$ concentration: 25 mg/L), available from Wako Pure Chemical Industries, Ltd., as a standard solution.

<Osmotic Pressure Measurement Method (Freezing Point Depression Method)>

The osmotic pressure of the culture supernatant was measured by a method utilizing a freezing point depression method as described below. The osmotic pressure value (mOsm/kg $H_2O$, abbreviated as mOsm) of the culture supernatant was measured by using an osmometer (Advanced Osmometer 3250, available from Advanced Instruments). Calibration was performed in low range mode (for 0 to 2000 mOsm) using 100 mOsm and 1500 mOsm standard solutions.

[Analysis of Polymer]

<$^1$H-NMR and $^{13}$C-NMR>

The chemical structure of the purified PHA (P(3HB)) obtained in Example 6 was analyzed by using a nuclear magnetic resonance spectrometer (ECA 500, JASCO Corporation). The purified PHA was dissolved in $CDCl_3$ in the concentration of 1.5 mass % and used as a measurement sample. The $^1$H-NMR spectrum was measured at 500 MHz at room temperature. The $^{13}$C-NMR spectrum was measured at 125 MHz at room temperature.

Figure 4:
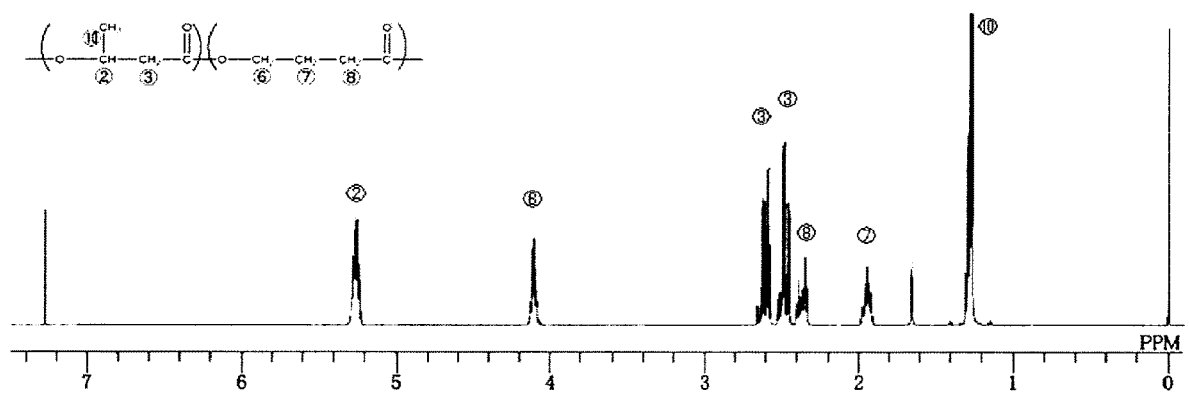
FIG. 4 shows $^1$H-NMR of PHA produced in Example 2.
Figure 5:
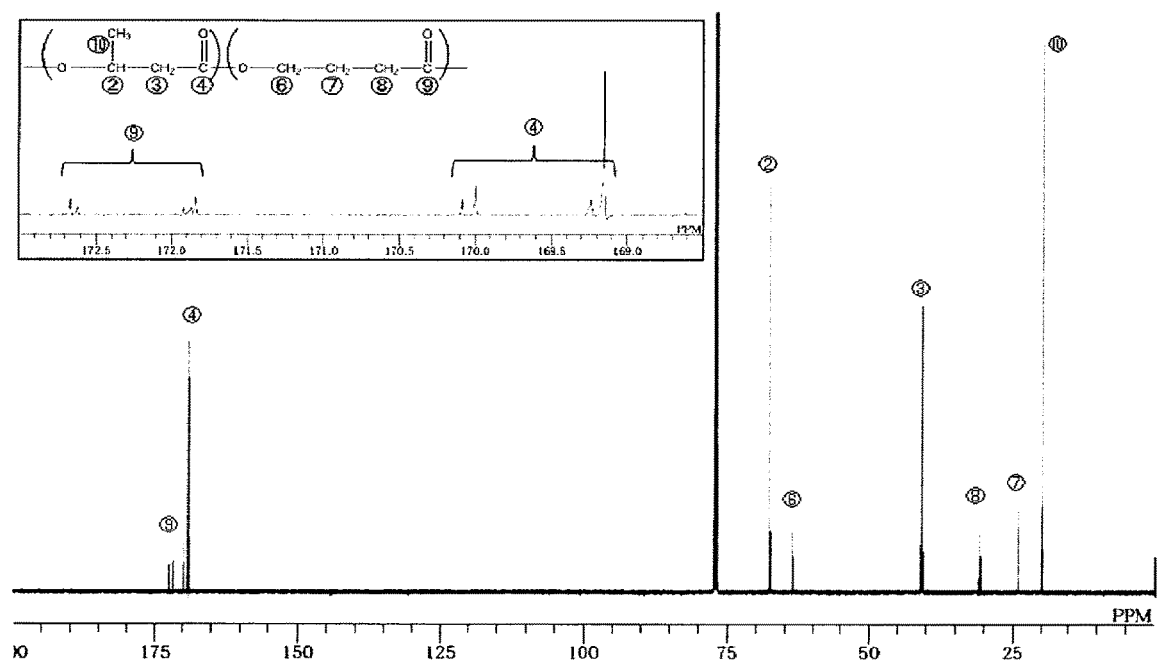
FIG. 5 shows $^{13}$C-NMR of PHA produced in Example 2.

The $^1$H-NMR of the PHA produced in Example 2 is shown in FIG. 4, and the $^{13}$C-NMR spectrum is shown in FIG. 5.

Figure 6:
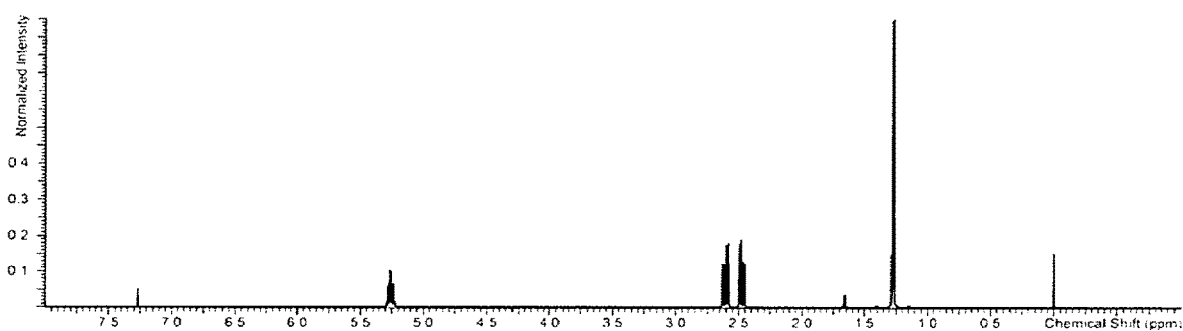
FIG. 6 shows $^1$H-NMR of P(3HB) produced in Example 6.
Figure 7:
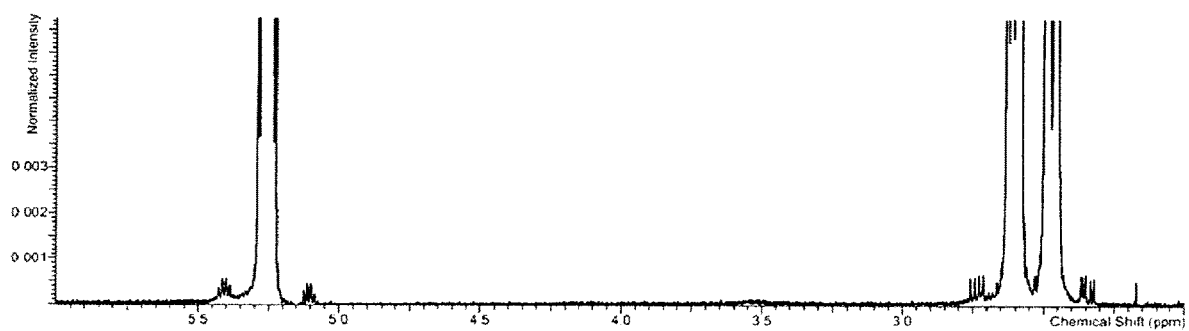
FIG. 7 shows a magnified view of FIG. 6.

The $^1$H-NMR spectrum comprising only the P(3HB) in Example 6 is shown in FIG. 6, and a magnified view of FIG. 6 is shown in FIG. 7.

The $^1$H-NMR spectra of the PHA extracted and purified from the culture solution three days after the start of the culture, obtained in Comparative Example 17, are shown in FIG. 8 and FIG. 9. FIG. 9 is a magnified view of FIG. 8. A magnified view of the $^1$H-NMR spectrum of the PHA extracted and purified from the culture solution five days after the start of the same culture is shown in FIG. 10. By the $^1$H-NMR analysis of P(3HB) obtained by growth-associated P(3HB) production of *Cupriavidus necator* H16 (ATCC17699) wild-type strain in the presence of PEG 200, the result showing the direct bonding between P(3HB) and PEG was obtained.

Examples 7 to 20 (Flask Culture)

Each PHA was produced by using *Cupriavidus necator* H16 (ATCC17699) by flask culture.

In each Erlenmeyer flask having a volumetric capacity of 500 mL containing 100 mL of a medium obtained by adding 8.86 g/L of fructose and 5.38 g/L of ε-caprolactone to the medium 1 (Examples 7 to 19; however, the ammonium sulfate and sodium chloride concentrations were in the amounts shown in the table) or a medium obtained by adding 8.86 g/L of fructose and 6.46 g/L of ε-caprolactone to the medium 1 (Example 20; however, the ammonium sulfate concentration was in the amount shown in the table), 1 mL of the preculture medium was inoculated and cultured at 30° C. and 150 rpm for the period of time shown in the table. The pH before the start of the culture was approximately from 6.8 to 7.5, and the pH at the termination of the culture was approximately from 5.7 to 6.2, which was weakly acidic. The pH during the culture was approximately from 5.7 to 7.5. After the termination of the culture, the bacterial cells were collected by centrifugal separation and lyophilized, and the weight of the dried bacterial cells was measured. Furthermore, the PHA contents determined by the GC method, the compositional analysis results, and the osmotic pressure measurement results are together shown in Table 27 below.

Each of the flask culture (batch culture) of Examples 7 to 20 satisfied the conditions where the osmotic pressure of the culture solution is from 200 mOsm to 900 mOsm and the nitrogen atom concentration of the culture solution is 0.30 g/L or greater at the initiation of the culture. During culture period that satisfied the conditions where the osmotic pressure of the culture solution is from 200 mOsm to 900 mOsm and the nitrogen atom concentration of the culture solution is 0.30 g/L or greater, a polyester having a weight average molecular weight of 1000000 or greater and comprising at least a 3-hydroxybutyrate unit as a polymerization unit was produced. Furthermore, in the flask culture (batch culture) of each of Examples 7 to 20, it is also anticipated that the osmotic pressure at the initiation of the culture was 200 mOsm or greater, while the osmotic pressure was reduced to less than 200 mOsm at the termination of the culture due to consumption of carbon source and other mineral components; however, even in this case, a polyester having a weight average molecular weight of 1000000 or greater and comprising at least a 3-hydroxybutyrate unit as a polymerization unit was produced.

[Results]

The analysis results of Examples 1 to 6, Comparative Examples 1 to 8 and 11 to 16, and Reference Examples 1 and 2 described above are shown below.

Frc: Fructose
ECL: ε-Caprolactone
GBL: γ-Butyrolactone
BD: 1,4-Butanediol
E/F: ε-Caprolactone/fructose ratio
G/F: γ-Butyrolactone/fructose ratio
B/F: 1,4-Butanediol/fructose ratio

TABLE 1

|  | Main carbon source | 4HB precursor | Carbon source ratio | Temperature | pH | pH adjusting solution | Ammonium sulfate g/L | NaCl (g/L) |
|---|---|---|---|---|---|---|---|---|
| Example 1 | Frc | ECL | E/F0.5 | 36 | 6 | 12.5% NH3 | 12.5 | 12.4 g/L in Frc solution |
| Example 2 | Frc | ECL | E/F0.5 | 36 | 6 | 12.5% NH3 | 10 | 2.5 g/L at initiation |
| Example 3 | Frc | ECL | E/F0.5 | 36 | 6 | 12.5% NH3 | 12.5 | |
| Comparative Example 1 | Frc | ECL | E/F0.5 | 36 | 6 | 12.5% NH3 | 7.5 | |
| Comparative Example 2 | Frc | ECL | E/F0.5 | 36 | 6 | 12.5% NH3 | 4 | |
| Comparative Example 3 | Frc | ECL | E/F0.5 | 36 | 6 | 4N NaOH | 12.5 | |
| Comparative Example 4 | Frc | ECL | E/F0.5 | 36 | 6 | 4N NaOH | 10 | |
| Comparative Example 5 | Frc | ECL | E/F0.5 | 36 | 6 | 4N NaOH | 7.5 | |
| Comparative Example 6 | Frc | ECL | E/F0.5 | 36 | 6.5 | 4N NaOH | 7.5 | |
| Comparative Example 7 | Frc | ECL | E/F0.5 | 36 | 7 | 4N NaOH | 7.5 | |
| Comparative Example 8 | Frc | ECL | E/F0.5 | 36 | 7.5 | 4N NaOH | 7.5 | |

|  | Bacterial cell concentration g/L | PHA content wt % | 4HB proportion mol % | $NH_4^+$ (g/L) | Osmotic pressure mOSM | $Mw \times 10^4$ Da | $Mn \times 10^4$ Da | Mw/Mn |
|---|---|---|---|---|---|---|---|---|
| Example 1 | 25.41 | 41.7 | 20.4 | 3.1 to 4.0 | 326 to 481 | 333 | 114 | 2.9 |
| Example 2 | 18.70 | 30.2 | 22.0 | 1.2 to 2.0 | 370 to 485 | 439 | 153 | 2.9 |
| Example 3 | 20.58 | 35.2 | 19.2 | 2.0 to 3.4 | 246 to 322 | 366 | 136 | 3.3 |
| Comparative Example 1 | 20.40 | 46.3 | 16.9 | 1.2 to 2.0 | 189 to 268 | 320 | 53 | 6.1 |
| Comparative Example 2 | 21.81 | 46.4 | 14.6 | 0.3 to 1.1 | 155 to 286 | 263 | 18 | 14.9 |
| Comparative Example 3 | 20.40 | 37.8 | 29.6 | 0 to 3.4 in final stage | 273 to 487 | 454 | 42 | 10.8 |
| Comparative Example 4 | 20.12 | 52.1 | 23.4 | 0 to 2.7 in middle stage | 223 to 473 | 289 | 27 | 10.8 |
| Comparative Example 5 | 18.54 | 56.9 | 22.4 | 0 to 2.1 in middle stage | 227 to 457 | 348 | 25 | 14.0 |
| Comparative Example 6 | 34.20 | 68.1 | 11.1 | Depletion (presumed) | — | 308 | 20 | 15.4 |
| Comparative Example 7 | 32.00 | 75.0 | 9.7 | Depletion (presumed) | — | 222 | 17 | 11.1 |
| Comparative Example 8 | 15.02 | 48.9 | 7.1 | Depletion (presumed) | — | 173 | 18 | 9.6 |

—: undetermined

TABLE 2

|  | Main carbon source | 4HB precursor | Carbon source ratio | Temperature | pH | pH adjustment | Ammonium sulfate g/L |
|---|---|---|---|---|---|---|---|
| Reference Example 1 | Frc | GBL | G/F0.5 | 36 | 6 | 12.5% NH3 | 12.5 |
| Reference Example 2 | Frc | GBL | G/F0.6 | 36 | 6 | 12.5% NH3 | 12.5 |
| Comparative Example 11 | Frc | GBL | G/F0.5 | 36 | 6 | 2N NaOH | 7.5 |
| Comparative Example 12 | Frc | BD | B/F0.7 | 36 | 6 | 12.5% NH3 | 12.5 |
| Comparative Example 13 | Frc | BD | B/F0.5 | 36 | 6 | 12.5% NH3 | 12.5 |
| Comparative Example 14 | Frc | BD | B/F0.5 | 36 | 6 | 2N NaOH | 7.5 |

TABLE 2-continued

|  | Bacterial cell concentration g/L | PHA content wt % | 4HB proportion mol % | NH4 g/L | Mw × $10^4$ Da | Mn × $10^4$ Da | Mw/Mn |
|---|---|---|---|---|---|---|---|
| Reference Example 1 | 15.73 | 18.3 | 23.8 | — | 236 | 50 | 4.7 |
| Reference Example 2 | 15.63 | 19.2 | 26.7 | — | 227 | 67 | 3.4 |
| Comparative Example 11 | 21.11 | 56.5 | 16.1 | Depletion (presumed) | 85 | 12 | 7.0 |
| Comparative Example 12 | 22.27 | 21.9 | 14.2 | — | 43 | 12 | 3.7 |
| Comparative Example 13 | 27.63 | 32.1 | 5.7 | — | 52 | 11 | 4.7 |
| Comparative Example 14 | 30.90 | 66.8 | 3.5 | Depletion (presumed) | 14 | 3 | 4.0 |

—: Undetermined

TABLE 3

| | Main carbon source | 4HB precursor | Temperature | pH | pH adjustment | Ammonium sulfate g/L | NaCl g/L | Bacterial cell concentration g/L |
|---|---|---|---|---|---|---|---|---|
| Example 4 | Frc | None | 36 | 6 | 12.5% NH3 | 12.5 | 12.4 g/L in Frc solution | 25.73 |
| Example 5 | Frc | None | 36 | 6 | 12.5% NH3 | 10 | 2.5 g/L at initiation | 35.75 |
| Example 6 | Frc | None | 36 | 6 | 12.5% NH3 | 12.5 | | 30.92 |
| Comparative Example 15 | Frc | None | 36 | 6 | 12.5% NH3 | 4 | | 20.25 |
| Comparative Example 16 | Frc | None | 36 | 6 | 4N NaOH | 4 | | 22.82 |

| | PHA content wt % | 4HB proportion mol % | NH4+ g/L | Osmotic pressure mOSM | Mw × $10^4$ Da | Mn × $10^4$ Da | Mw/Mn |
|---|---|---|---|---|---|---|---|
| Example 4 | 32.6 | 0 | 2.2 to 3.2 | 307 to 324 | 228 | 91 | 2.5 |
| Example 5 | 48.5 | 0 | 1.4 to 2.7 | 233 to 372 | 239 | 81 | 3.0 |
| Example 6 | 51.9 | 0 | 2.0 to 3.5 | 203 to 323 | 193 | 80 | 2.4 |
| Comparative Example 15 | 30.8 | 0 | 0.4 to 1.1 | 141 to 203 | 138 | 41 | 3.5 |
| Comparative Example 16 | 74.7 | 0 | 0 to 1.0 at initiation | 149 to 284 | 127 | 27 | 4.7 |

The analysis results for each culture time of Examples 1 to 6, Comparative Examples 1 to 8 and 11 to 17, and Reference Examples 1 and 2 are shown below.
DCW: Dry cell weight
RB: Residual biomass
E/F: ε-Caprolactone/fructose ratio
G/F: γ-Butyrolactone/fructose ratio
B/F: 1,4-Butanediol/fructose ratio

TABLE 4

| Example 1: | | | | | | | | | | |
|---|---|---|---|---|---|---|---|---|---|---|
| Culture time | DCW | RB | PHA Content | 4HB Ratio | | NH4+ | Osmotic pressure | Molecular weight (×$10^6$) | | |
| Hr | g/L | g/L | % | % | E/F | g/L | mOSM | Mw | Mn | Mw/Mn |
| 0 | | | | | 0.48 | 3.25 | 326 | | | |
| 16.7 | 3.36 | 2.34 | 30.2 | 10.6 | 0.48 | 3.60 | 331 | 3.32 | 1.52 | 2.19 |
| 39.9 | 8.90 | 6.69 | 24.8 | 19.7 | 0.49 | 3.55 | 342 | 3.50 | 1.39 | 2.51 |
| 66.2 | 17.47 | 12.36 | 29.2 | 24.8 | 0.50 | 3.12 | 344 | 3.35 | 1.20 | 2.79 |
| 90.2 | 24.22 | 16.26 | 32.9 | 22.6 | 0.50 | 3.20 | 357 | 3.34 | 1.26 | 2.64 |
| 114.8 | 25.31 | 16.06 | 36.6 | 19.2 | 0.51 | 3.22 | 400 | 3.50 | 1.12 | 3.13 |
| 140.2 | 25.41 | 14.82 | 41.7 | 20.4 | 0.51 | 3.21 | 481 | 3.33 | 1.14 | 2.92 |

TABLE 5

| | | | | Example 2: | | | | | | |
|---|---|---|---|---|---|---|---|---|---|---|
| Culture time | DCW | RB | PHA Content | 4HB Ratio | | NH4+ | Osmotic pressure | Molecular weight (x10^6) | | |
| Hr | g/L | g/L | % | % | E/F | g/L | mOSM | Mw | Mn | Mw/Mn |
| 0 | | | | | 0.48 | 2.74 | 370 | | | |
| 20.1 | 4.22 | 2.67 | 36.8 | 11.1 | 0.51 | 2.20 | 382 | 3.88 | 2.09 | 1.85 |
| 39.5 | 7.86 | 5.41 | 31.2 | 17.1 | 0.49 | 2.31 | 370 | 3.98 | 1.42 | 2.81 |
| 63.7 | 13.59 | 9.83 | 27.6 | 25.6 | 0.51 | 2.40 | 394 | 4.25 | 1.76 | 2.41 |
| 91.4 | 17.65 | 12.26 | 30.5 | 24.2 | 0.52 | 2.26 | 364 | 4.44 | 1.28 | 3.47 |
| 112.0 | 18.58 | 13.05 | 29.7 | 21.2 | 0.52 | 2.30 | 380 | 4.49 | 1.63 | 2.76 |
| 140.2 | 18.70 | 13.06 | 30.2 | 22.0 | 0.52 | 2.39 | 485 | 4.39 | 1.53 | 2.87 |

TABLE 6

| | | | | Example 3: | | | | | | |
|---|---|---|---|---|---|---|---|---|---|---|
| Culture time | DCW | RB | PHA Content | 4HB Ratio | | NH4+ | Osmotic pressure | Molecular weight (x10^6) | | |
| Hr | g/L | g/L | % | % | E/F | g/L | mOSM | Mw | Mn | Mw/Mn |
| 0 | | | | | 0.48 | 3.40 | 322 | | | |
| 16.4 | 4.18 | 2.65 | 36.7 | 9.2 | 0.49 | 3.00 | 342 | 2.46 | 1.12 | 2.19 |
| 42.5 | 10.61 | 7.86 | 25.9 | 19.5 | 0.51 | 2.52 | 300 | 2.69 | 1.12 | 2.40 |
| 61.7 | 16.97 | 12.14 | 28.5 | 23.9 | 0.51 | 2.81 | 309 | 3.16 | 0.93 | 3.42 |
| 75.5 | 18.42 | 13.14 | 28.7 | 21.9 | 0.52 | 2.33 | 272 | 3.32 | 1.32 | 2.52 |
| 88.1 | 20.01 | 14.21 | 29.0 | 19.9 | 0.52 | 2.20 | 281 | 3.36 | 1.22 | 2.76 |
| 100.0 | 20.58 | 13.33 | 35.2 | 19.2 | 0.52 | 2.06 | 246 | 3.42 | 1.05 | 3.27 |

TABLE 7

| | | | | Comparative Example 1: | | | | | | |
|---|---|---|---|---|---|---|---|---|---|---|
| Culture time | DCW | RB | PHA Content | 4HB Ratio | | NH4+ | Osmotic pressure | Molecular weight (x10^6) | | |
| Hr | g/L | g/L | % | % | E/F | g/L | mOSM | Mw | Mn | Mw/Mn |
| 0 | | | | | 0.48 | 2.00 | 242 | | | |
| 15.5 | 3.97 | 2.66 | 32.9 | 8.9 | 0.47 | 1.62 | 259 | 3.01 | 1.36 | 2.22 |
| 27.0 | 6.77 | 4.93 | 27.3 | 13.2 | 0.5 | 1.42 | 245 | 3.18 | 1.28 | 2.48 |
| 39.0 | 9.88 | 7.28 | 26.3 | 18.5 | 0.51 | 1.67 | 268 | 3.42 | 1.26 | 2.70 |
| 50.5 | 13.07 | 9.92 | 24.1 | 23.2 | 0.51 | 1.53 | 249 | 3.48 | 1.29 | 2.71 |
| 62.5 | 16.24 | 12.29 | 24.3 | 24.6 | 0.51 | 1.40 | 225 | 3.39 | 1.08 | 3.13 |
| 71.5 | 17.25 | 12.44 | 27.9 | 23.2 | 0.51 | 1.41 | 233 | 3.51 | 0.97 | 3.60 |
| 84.5 | 17.95 | 12.50 | 30.4 | 20.4 | 0.51 | 1.40 | 189 | 3.48 | 0.93 | 3.74 |
| 98.0 | 18.86 | 12.01 | 36.3 | 18.1 | 0.51 | 1.50 | 244 | 3.13 | 0.62 | 5.06 |
| 110.0 | 20.40 | 12.67 | 37.9 | 16.5 | 0.51 | 1.23 | 221 | 3.22 | 0.55 | 5.84 |
| 122.5 | 21.72 | 11.66 | 46.3 | 16.9 | 0.52 | 1.52 | 252 | 3.20 | 0.53 | 6.05 |

TABLE 8

| | | | | Comparative Example 2: | | | | | | |
|---|---|---|---|---|---|---|---|---|---|---|
| Culture time | DCW | RB | PHA Content | 4HB Ratio | | NH4+ | Osmotic pressure | Molecular weight (x10^6) | | |
| hr | g/L | g/L | % | % | E/F | g/L | mOSM | Mw | Mn | Mw/Mn |
| 0 | | | | | 0.48 | 1.09 | 191 | | | |
| 17.9 | 4.05 | 2.99 | 26.2 | 7.7 | 0.46 | 0.60 | 200 | 2.92 | 1.13 | 2.59 |
| 30.4 | 7.50 | 5.77 | 23.0 | 15.9 | 0.47 | 0.59 | 197 | 2.91 | 1.01 | 2.89 |
| 42.1 | 11.60 | 9.17 | 21.0 | 23.6 | 0.49 | 0.60 | 191 | 3.04 | 0.90 | 3.39 |
| 54.5 | 16.13 | 12.98 | 19.5 | 20.8 | 0.50 | 0.47 | 155 | 2.95 | 0.85 | 3.46 |
| 68.6 | 18.22 | 13.17 | 27.7 | 21.0 | 0.50 | 0.33 | 162 | 2.25 | 0.22 | 10.13 |
| 79.0 | 19.97 | 12.02 | 39.8 | 17.1 | 0.50 | 0.60 | 181 | 2.14 | 0.19 | 11.41 |
| 92.0 | 22.03 | 12.31 | 44.1 | 13.9 | 0.51 | 0.64 | 187 | 2.32 | 0.20 | 11.44 |
| 102.5 | 22.09 | 11.60 | 47.5 | 14.7 | 0.51 | 0.90 | 265 | 2.51 | 0.20 | 12.67 |

TABLE 8-continued

Comparative Example 2:

| Culture time | DCW | RB | PHA Content | 4HB Ratio | | NH4+ | Osmotic pressure | Molecular weight (×10⁶) | | |
|---|---|---|---|---|---|---|---|---|---|---|
| hr | g/L | g/L | % | % | E/F | g/L | mOSM | Mw | Mn | Mw/Mn |
| 116.0 | 21.91 | 11.64 | 46.9 | 14.6 | 0.51 | 0.80 | 240 | 2.53 | 0.19 | 13.36 |
| 125.5 | 21.71 | 11.63 | 46.4 | 14.6 | 0.51 | 0.96 | 286 | 2.63 | 0.18 | 14.94 |

TABLE 9

Comparative Example 3:

| Culture time | DCW | RB | PHA Content | 4HB Ratio | | NH4+ | Osmotic pressure | Molecular weight (×10⁶) | | |
|---|---|---|---|---|---|---|---|---|---|---|
| Hr | g/L | g/L | % | % | E/F | g/L | mOSM | Mw | Mn | Mw/Mn |
| 0 | | | | | 0.48 | 3.40 | 305 | | | |
| 15.7 | 2.94 | 1.77 | 39.8 | 9.1 | 0.50 | 2.26 | 317 | 3.31 | 1.22 | 2.71 |
| 39.2 | 7.75 | 5.08 | 34.4 | 15.2 | 0.51 | 1.68 | 273 | 3.73 | 1.21 | 3.07 |
| 64.5 | 11.64 | 8.19 | 29.6 | 21.7 | 0.51 | 1.57 | 358 | 4.42 | 0.91 | 4.84 |
| 88.5 | 15.48 | 10.27 | 33.7 | 30.0 | 0.51 | 0.83 | 333 | 4.67 | 1.03 | 4.52 |
| 112.5 | 19.09 | 12.95 | 32.2 | 24.3 | 0.51 | 0.36 | 343 | 5.06 | 0.99 | 5.12 |
| 136.5 | 19.85 | 12.45 | 37.3 | 25.9 | 0.51 | 0.15 | 347 | 4.72 | 0.66 | 7.14 |
| 160.5 | 19.99 | 12.83 | 35.8 | 26.5 | 0.52 | 0.05 | 414 | 4.62 | 0.61 | 7.62 |
| 173.3 | 20.40 | 12.69 | 37.8 | 29.6 | 0.52 | 0.00 | 487 | 4.54 | 0.42 | 10.8 |

TABLE 10

Comparative Example 4:

| Culture time | DCW | RB | PHA Content | 4HB Ratio | | NH4+ | Osmotic pressure | Molecular weight (×10⁶) | | |
|---|---|---|---|---|---|---|---|---|---|---|
| hr | g/L | g/L | % | % | E/F | g/L | mOSM | Mw | Mn | Mw/Mn |
| 0 | | | | | 0.48 | 2.79 | 288 | | | |
| 21.5 | 4.48 | 3.01 | 32.9 | 8.9 | 0.49 | 1.65 | 223 | 3.62 | 1.27 | 2.85 |
| 32.0 | 6.58 | 4.69 | 28.7 | 13.7 | 0.50 | 1.35 | 307 | 4.12 | 1.27 | 3.25 |
| 49.0 | 10.02 | 7.36 | 26.5 | 21.3 | 0.50 | 1.08 | 313 | 4.51 | 0.94 | 4.78 |
| 67.0 | 13.91 | 10.61 | 23.8 | 28.2 | 0.50 | 0.32 | 296 | 4.53 | 0.92 | 4.94 |
| 92.0 | 16.46 | 10.64 | 35.3 | 25.7 | 0.51 | 0.02 | 288 | 4.74 | 0.78 | 6.09 |
| 116.5 | 19.29 | 9.79 | 49.2 | 23.3 | 0.51 | 0 | 294 | 3.78 | 0.58 | 6.47 |
| 140.5 | 20.12 | 9.63 | 52.1 | 23.4 | 0.51 | 0 | 305 | 2.89 | 0.27 | 10.8 |

TABLE 11

Comparative Example 5:

| Culture time | DCW | RB | PHA Content | 4HB Ratio | | NH4+ | Osmotic pressure | Molecular weight (×10⁶) | | |
|---|---|---|---|---|---|---|---|---|---|---|
| hr | g/L | g/L | % | % | E/F | g/L | mOSM | Mw | Mn | Mw/Mn |
| 0 | | | | | 0.48 | 2.06 | 227 | | | |
| 21.5 | 4.44 | 3.04 | 31.5 | 9.2 | 0.43 | 1.31 | 251 | 3.69 | 1.07 | 3.44 |
| 32 | 6.78 | 4.77 | 29.6 | 13.8 | 0.43 | 0.99 | 273 | 3.96 | 1.13 | 3.51 |
| 49 | 10.64 | 7.65 | 28.1 | 21.3 | 0.48 | 0.31 | 270 | 4.55 | 1.03 | 4.42 |
| 67 | 13.96 | 9.15 | 34.4 | 22.4 | 0.49 | 0.00 | 267 | 5.34 | 1.14 | 4.69 |
| 92 | 17.82 | 8.49 | 52.4 | 20.1 | 0.5 | 0.00 | 266 | 4.89 | 0.80 | 6.10 |
| 116.5 | 19.93 | 9.44 | 52.7 | 21.0 | 0.51 | 0.00 | 270 | 4.07 | 0.51 | 8.02 |
| 140.5 | 19.25 | 8.25 | 57.2 | 22.9 | 0.51 | 0.00 | 375 | 3.74 | 0.35 | 10.7 |
| 165.5 | 18.54 | 7.99 | 56.9 | 22.4 | 0.52 | 0.00 | 457 | 3.48 | 0.25 | 14.0 |

TABLE 12

Comparative Example 6:

| Culture time | DCW | RB | PHA Content | 4HB Ratio | | NH4+ | Osmotic pressure | Molecular weight (×10⁶) | | |
|---|---|---|---|---|---|---|---|---|---|---|
| hr | g/L | g/L | % | % | E/F | g/L | mOSM | Mw | Mn | Mw/Mn |
| 0 | | | | | 0.36 | | | | | |
| 20.5 | 4.73 | 3.31 | 29.9 | 8.2 | 0.49 | | | 3.95 | 1.54 | 5.07 |
| 31.5 | 8.14 | 6.01 | 26.2 | 11.2 | 0.50 | | | 4.22 | 1.43 | 6.07 |
| 52.0 | 17.76 | 10.31 | 41.9 | 11.7 | 0.51 | | | 5.02 | 1.63 | 7.07 |
| 67.0 | 22.89 | 10.94 | 52.2 | 11.4 | 0.51 | | | 4.67 | 1.23 | 8.07 |
| 92.0 | 30.78 | 12.07 | 60.8 | 11.5 | 0.51 | | | 4.22 | 0.54 | 9.07 |
| 104.0 | 33.68 | 11.67 | 65.3 | 11.7 | 0.51 | | | 3.72 | 0.46 | 10.1 |
| 122.0 | 34.20 | 10.91 | 68.1 | 11.1 | 0.51 | | | 3.08 | 0.20 | 11.1 |

TABLE 13

Comparative Example 7:

| Culture time | DCW | RB | PHA | 4HB | | NH4+ | Osmotic pressure | Molecular weight (×10⁶) | | |
|---|---|---|---|---|---|---|---|---|---|---|
| Hr | g/L | g/L | Content % | Ratio % | E/F | g/L | mOSM | Mw | Mn | Mw/Mn |
| 0 | | | | | 0.48 | | | | | |
| 19.0 | 3.61 | 2.37 | 34.5 | 12.0 | 0.48 | | | 3.53 | 1.27 | 5.07 |
| 41.5 | 11.49 | 7.54 | 34.3 | 15.5 | 0.51 | | | 3.81 | 1.10 | 6.07 |
| 65.4 | 21.17 | 10.14 | 52.1 | 11.1 | 0.52 | | | 3.81 | 0.93 | 7.07 |
| 77.4 | | | | | 0.52 | | | 3.75 | 0.86 | 8.07 |
| 92.2 | 29.48 | 11.42 | 61.3 | 11.0 | 0.52 | | | 3.40 | 0.55 | 9.07 |
| 115.5 | 34.92 | 10.99 | 68.5 | 10.7 | 0.52 | | | 2.76 | 0.25 | 10.1 |
| 137.5 | 32.00 | 8.00 | 75.0 | 9.7 | 0.56 | | | 2.22 | 0.17 | 11.1 |

TABLE 14

Comparative Example 8:

| Culture time | DCW | RB | PHA | 4HB | | NH4+ | Osmotic pressure | Molecular weight (×10⁶) | | |
|---|---|---|---|---|---|---|---|---|---|---|
| hr | g/L | g/L | Content % | Ratio % | E/F | g/L | mOSM | Mw | Mn | Mw/Mn |
| 0 | | | | | 0.36 | | | | | |
| 31.5 | 4.13 | 3.03 | 26.7 | 12.7 | 0.46 | | | 2.75 | 0.87 | 5.07 |
| 52.0 | 7.19 | 5.97 | 17.0 | 15.7 | 0.49 | | | 2.28 | 0.47 | 6.07 |
| 67.0 | 10.82 | 9.17 | 15.3 | 16.2 | 0.49 | | | 2.05 | 0.36 | 7.07 |
| 92.0 | 12.83 | 10.04 | 21.7 | 15.6 | 0.50 | | | 1.83 | 0.40 | 8.07 |
| 122.0 | 17.31 | 9.59 | 44.6 | 12.3 | 0.51 | | | 1.91 | 0.34 | 9.07 |
| 141.0 | 15.68 | 8.05 | 48.7 | 8.1 | 0.51 | | | 1.80 | 0.20 | 10.1 |
| 149.0 | 15.02 | 7.67 | 48.9 | 7.1 | 0.51 | | | 1.73 | 0.18 | 11.1 |

TABLE 15

Reference Example 1:

| Culture time | DCW | RB | PHA | 4HB | | NH4+ | Osmotic pressure | Molecular weight (×10⁶) | | |
|---|---|---|---|---|---|---|---|---|---|---|
| Hr | g/L | g/L | Content % | Ratio % | G/F | g/L | mOSM | Mw | Mn | Mw/Mn |
| 0 | | | | | 0.48 | | | | | |
| 21.6 | 4.65 | 3.74 | 19.6 | 2.9 | 0.48 | | | 2.23 | 0.77 | 2.89 |
| 45.3 | 10.34 | 8.91 | 13.9 | 13.9 | 0.51 | | | 1.72 | 0.52 | 3.29 |
| 66.7 | 14.89 | 12.64 | 15.1 | 21.5 | 0.51 | | | 2.36 | 0.60 | 3.91 |
| 93.0 | 15.45 | 12.82 | 17.0 | 22.0 | 0.52 | | | 2.55 | 0.57 | 4.45 |
| 105.0 | 15.73 | 12.85 | 18.3 | 23.8 | 0.52 | | | 2.36 | 0.50 | 4.71 |

TABLE 16

| | | | | Reference Example 2: | | | | | | |
|---|---|---|---|---|---|---|---|---|---|---|
| Culture time | DCW | RB | PHA | 4HB | | NH4+ | Osmotic pressure | Molecular weight (×10⁶) | | |
| Hr | g/L | g/L | Content % | Ratio % | G/F | g/L | mOSM | Mw | Mn | Mw/Mn |
| 0 | | | | | 0.48 | | | | | |
| 21.6 | 4.68 | 3.72 | 20.6 | 2.7 | 0.50 | | | 2.20 | 0.77 | 2.85 |
| 45.3 | 10.58 | 8.81 | 16.7 | 17.5 | 0.56 | | | 1.85 | 0.64 | 2.92 |
| 66.7 | 15.03 | 12.59 | 16.2 | 23.7 | 0.58 | | | 2.23 | 0.63 | 3.52 |
| 93.0 | 15.38 | 12.63 | 17.9 | 24.6 | 0.60 | | | 2.38 | 0.53 | 4.51 |
| 105.0 | 15.63 | 12.64 | 19.2 | 26.7 | 0.60 | | | 2.27 | 0.67 | 3.40 |

TABLE 17

| | | | | Comparative Example 11: | | | | | | |
|---|---|---|---|---|---|---|---|---|---|---|
| Culture time | DCW | RB | PHA | 4HB | | NH4+ | Osmotic pressure | Molecular weight (×10⁶) | | |
| hr | g/L | g/L | Content % | Ratio % | G/F | g/L | mOSM | Mw | Mn | Mw/Mn |
| 0 | | | | | 0.48 | | | | | |
| 20.7 | 5.11 | 4.05 | 20.7 | 3.4 | 0.36 | | | | | |
| 30.5 | 7.73 | 6.18 | 20.0 | 5.8 | 0.41 | | | | | |
| 44.6 | 11.86 | 9.84 | 17.1 | 15.5 | 0.45 | | | | | |
| 54.5 | 14.27 | 10.19 | 28.6 | 18.0 | 0.46 | | | | | |
| 69.0 | 17.28 | 10.04 | 41.9 | 18.2 | 0.47 | | | | | |
| 78.5 | 19.08 | 9.50 | 50.2 | 18.8 | 0.48 | | | | | |
| 92.0 | 21.14 | 9.66 | 54.3 | 18.5 | 0.49 | | | | | |
| 116.0 | 23.44 | 9.81 | 58.2 | 17.0 | 0.49 | | | | | |
| 141.0 | 22.67 | 8.53 | 62.4 | 16.0 | 0.49 | | | | | |
| 165.0 | 21.11 | 9.19 | 56.5 | 16.1 | 0.50 | | | 0.85 | 0.12 | 7.04 |

TABLE 18

| | | | | Comparative Example 12: | | | | | | |
|---|---|---|---|---|---|---|---|---|---|---|
| Culture time | DCW | RB | PHA | 4HB | | NH4+ | Osmotic pressure | Molecular weight (×10⁶) | | |
| hr | g/L | g/L | Content % | Ratio % | B/F | g/L | mOSM | Mw | Mn | Mw/Mn |
| 0 | | | | | 0.48 | | | | | |
| 18.5 | 3.82 | 3.15 | 17.4 | 0.5 | 0.75 | | | 0.62 | 0.14 | 4.53 |
| 42.5 | 8.54 | 7.23 | 15.3 | 2.6 | 0.73 | | | 0.42 | 0.11 | 3.82 |
| 73.3 | 16.14 | 14.30 | 11.4 | 10.0 | 0.71 | | | 0.39 | 0.14 | 2.89 |
| 101.4 | 18.24 | 15.12 | 17.1 | 11.0 | 0.71 | | | 0.48 | 0.12 | 3.88 |
| 120.7 | 20.18 | 16.83 | 16.6 | 13.0 | 0.71 | | | 0.41 | 0.08 | 5.20 |
| 145.2 | 21.37 | 18.03 | 15.6 | 13.2 | 0.70 | | | 0.54 | 0.11 | 5.04 |
| 166.8 | 2L79 | 17.30 | 20.6 | 12.5 | 0.70 | | | 0.50 | 0.11 | 4.73 |
| 191.3 | 21.51 | 17.31 | 19.5 | 12.4 | 0.70 | | | 0.39 | 0.11 | 3.57 |
| 208.5 | 22.27 | 17.38 | 21.9 | 14.2 | 0.70 | | | 0.43 | 0.12 | 3.65 |

TABLE 19

| | | | | Comparative Example 13: | | | | | | |
|---|---|---|---|---|---|---|---|---|---|---|
| Culture time | DCW | RB | PHA | 4HB | | NH4+ | Osmotic pressure | Molecular weight (×10⁶) | | |
| hr | g/L | g/L | Content % | Ratio % | B/F | g/L | mOSM | Mw | Mn | Mw/Mn |
| 0 | | | | | 0.48 | | | | | |
| 18.5 | 4.08 | 3.34 | 18.1 | 0.3 | 0.50 | | | 0.80 | 0.16 | 5.07 |
| 42.5 | 9.38 | 7.92 | 15.6 | 2.6 | 0.52 | | | 0.52 | 0.15 | 3.51 |
| 73.3 | 17.46 | 15.09 | 13.6 | 8.2 | 0.52 | | | 0.47 | 0.13 | 3.54 |
| 101.4 | 20.17 | 15.69 | 22.2 | 7.8 | 0.52 | | | 0.56 | 0.11 | 5.30 |
| 120.7 | 22.07 | 16.36 | 25.9 | 7.2 | 0.52 | | | 0.61 | 0.14 | 4.49 |
| 145.2 | 25.67 | 18.37 | 28.4 | 6.2 | 0.52 | | | 0.57 | 0.17 | 3.33 |

TABLE 19-continued

Comparative Example 13:

| Culture time | DCW | RB | PHA | 4HB | | NH4+ | Osmotic pressure | Molecular weight (×10⁶) | | |
|---|---|---|---|---|---|---|---|---|---|---|
| hr | g/L | g/L | Content % | Ratio % | B/F | g/L | mOSM | Mw | Mn | Mw/Mn |
| 166.8 | 25.50 | 19.01 | 25.5 | 6.4 | 0.52 | | | 0.58 | 0.16 | 3.57 |
| 191.3 | 26.45 | 19.06 | 28.0 | 6.3 | 0.52 | | | 0.50 | 0.13 | 3.81 |
| 208.5 | 27.63 | 18.75 | 32.1 | 5.7 | 0.52 | | | 0.52 | 0.11 | 4.69 |

TABLE 20

Comparative Example 14:

| Culture time | DCW | RB | PHA | 4HB | | NH4+ | Osmotic pressure | Molecular weight (×10⁶) | | |
|---|---|---|---|---|---|---|---|---|---|---|
| hr | g/L | g/L | Content % | Ratio % | B/F | g/L | mOSM | Mw | Mn | Mw/Mn |
| 0 | | | | | 0.48 | | | | | |
| 20.7 | 5.23 | 4.17 | 20.2 | 3.0 | 0.47 | | | | | |
| 30.5 | 7.80 | 6.40 | 18.0 | 3.0 | 0.47 | | | | | |
| 44.6 | 12.24 | 10.36 | 15.4 | 5.7 | 0.47 | | | | | |
| 54.5 | 15.08 | 10.59 | 29.8 | 5.8 | 0.48 | | | | | |
| 69.0 | 18.80 | 10.28 | 45.3 | 5.7 | 0.49 | | | | | |
| 78.5 | 21.30 | 10.40 | 51.2 | 5.6 | 0.49 | | | | | |
| 92.0 | 24.55 | 10.75 | 56.2 | 5.3 | 0.50 | | | | | |
| 116.0 | 29.15 | 10.36 | 64.5 | 4.9 | 0.50 | | | | | |
| 141.0 | 32.00 | 10.38 | 67.6 | 4.2 | 0.50 | | | | | |
| 165.0 | 32.54 | 10.74 | 67.0 | 3.8 | 0.51 | | | | | |
| 189.5 | 30.90 | 10.25 | 66.8 | 3.5 | 0.51 | | | 0.14 | 0.03 | 4.04 |

TABLE 21

Example 4:

| Culture time | DCW | RB | PHA | 4HB | | NH4+ | Osmotic pressure | Molecular weight (×10⁶) | | |
|---|---|---|---|---|---|---|---|---|---|---|
| hr | g/L | g/L | Content % | Ratio % | E/F | g/L | mOSM | Mw | Mn | Mw/Mn |
| 0 | | | | | 0 | 3.21 | 324 | | | |
| 16.7 | 2.49 | 1.83 | 26.6 | 0 | 0 | 3.12 | 313 | 3.08 | 1.18 | 2.62 |
| 39.9 | 5.26 | 4.11 | 21.8 | 0 | 0 | 3.05 | 319 | 2.40 | 1.00 | 2.40 |
| 66.2 | 9.85 | 7.78 | 21.0 | 0 | 0 | 2.81 | 312 | 2.09 | 0.78 | 2.69 |
| 90.2 | 15.73 | 12.63 | 19.7 | 0 | 0 | 2.73 | 305 | 1.98 | 0.86 | 2.29 |
| 114.8 | 18.51 | 13.38 | 27.7 | 0 | 0 | 2.54 | 311 | 2.21 | 0.96 | 2.30 |
| 140.2 | 21.29 | 14.98 | 29.6 | 0 | 0 | 2.24 | 311 | 2.22 | 0.84 | 2.64 |
| 161.7 | 23.55 | 15.69 | 33.4 | 0 | 0 | 2.33 | 320 | 2.24 | 0.99 | 2.27 |
| 185.2 | 25.73 | 17.34 | 32.6 | 0 | 0 | 2.16 | 321 | 2.28 | 0.91 | 2.51 |

TABLE 22

Example 5:

| Culture time | DCW | RB | PHA | 4HB | | NH4+ | Osmotic pressure | Molecular weight (×10⁶) | | |
|---|---|---|---|---|---|---|---|---|---|---|
| Hr | g/L | g/L | Content % | Ratio % | E/F | g/L | mOSM | Mw | Mn | Mw/Mn |
| 0 | | | | | 0 | 2.73 | 372 | | | |
| 20.1 | 4.54 | 3.44 | 24.2 | 0 | 0 | 2.24 | 341 | 3.19 | 1.26 | 2.53 |
| 39.5 | 9.38 | 7.31 | 22.0 | 0 | 0 | 2.09 | 323 | 2.60 | 1.01 | 2.58 |
| 63.7 | 16.73 | 12.89 | 22.9 | 0 | 0 | 1.95 | 310 | 2.37 | 0.97 | 2.44 |
| 91.4 | 20.54 | 13.43 | 34.6 | 0 | 0 | 1.88 | 288 | 2.24 | 0.78 | 2.86 |
| 112.0 | 24.47 | 13.56 | 44.6 | 0 | 0 | 1.70 | 276 | 2.25 | 0.86 | 2.64 |
| 140.2 | 29.03 | 15.80 | 45.6 | 0 | 0 | 1.57 | 254 | 2.31 | 0.89 | 2.61 |
| 159.9 | 31.80 | 17.14 | 46.1 | 0 | 0 | 1.53 | 254 | 2.37 | 0.88 | 2.68 |
| 185.9 | 35.75 | 18.41 | 48.5 | 0 | 0 | 1.35 | 233 | 2.39 | 0.81 | 2.96 |

TABLE 23

Example 6:

| Culture time | DCW | RB | PHA | | 4HB | NH4+ | Osmotic pressure | Molecular weight (×10⁶) | | |
|---|---|---|---|---|---|---|---|---|---|---|
| Hr | g/L | g/L | Content % | Ratio % | E/F | g/L | mOSM | Mw | Mn | Mw/Mn |
| 0 | | | | | 0 | 3.45 | 323 | | | |
| 22.0 | 3.83 | 2.94 | 23.4 | 0 | 0 | 3.00 | 303 | 2.45 | 1.01 | 2.43 |
| 36.2 | 7.95 | 6.31 | 20.6 | 0 | 0 | 2.93 | 302 | 2.05 | 0.85 | 2.40 |
| 48.0 | 13.73 | 11.50 | 16.2 | 0 | 0 | 2.83 | 283 | 1.86 | 0.76 | 2.46 |
| 57.5 | 17.27 | 13.58 | 21.4 | 0 | 0 | 2.36 | 276 | 1.88 | 0.78 | 2.41 |
| 72.0 | 20.49 | 13.79 | 32.7 | 0 | 0 | 2.62 | 270 | 1.99 | 0.83 | 2.41 |
| 84.0 | 23.40 | 13.93 | 40.5 | 0 | 0 | 2.83 | 253 | 2.04 | 0.84 | 2.42 |
| 96.5 | 26.38 | 15.13 | 42.6 | 0 | 0 | 2.71 | 256 | 1.97 | 0.85 | 2.32 |
| 108.0 | 28.84 | 14.83 | 48.6 | 0 | 0 | 2.56 | 246 | 1.97 | 0.80 | 2.45 |
| 116.8 | 30.92 | 15.32 | 50.4 | 0 | 0 | 2.53 | 235 | 1.96 | 0.83 | 2.37 |
| 131.9 | 33.72 | 15.83 | 53.1 | 0 | 0 | 2.61 | 237 | 1.91 | 0.73 | 2.63 |
| 144.0 | 36.17 | 17.02 | 53.0 | 0 | 0 | 2.00 | 203 | 1.96 | 0.85 | 2.31 |
| 150.0 | 37.67 | 18.10 | 51.9 | 0 | 0 | 2.20 | 209 | 1.93 | 0.80 | 2.41 |

TABLE 24

Comparative Example 15:

| Culture time | DCW | RB | PHA | | 4HB | NH4+ | Osmotic pressure | Molecular weight (×10⁶) | | |
|---|---|---|---|---|---|---|---|---|---|---|
| Hr | g/L | g/L | Content % | Ratio % | E/F | g/L | mOSM | Mw | Mn | Mw/Mn |
| 0 | | | | | 0 | 1.09 | 196 | | | |
| 22.0 | 4.48 | 3.67 | 18.2 | 0 | 0 | 0.62 | 165 | 2.31 | 0.89 | 2.59 |
| 36.2 | 8.90 | 7.70 | 13.5 | 0 | 0 | 0.51 | 155 | 1.84 | 0.68 | 2.72 |
| 48.0 | 14.78 | 13.03 | 11.8 | 0 | 0 | 0.45 | 150 | 1.59 | 0.68 | 2.36 |
| 57.5 | 16.87 | 13.35 | 20.9 | 0 | 0 | 0.47 | 141 | 1.16 | 0.38 | 3.06 |
| 72.0 | 20.25 | 14.02 | 30.8 | 0 | 0 | 0.41 | 157 | 1.17 | 0.34 | 3.47 |

TABLE 25

Comparative Example 16:

| Culture time | DCW | RB | PHA | | 4HB | NH4+ | Osmotic pressure | Molecular weight (×10⁶) | | |
|---|---|---|---|---|---|---|---|---|---|---|
| Hr | g/L | g/L | Content % | Ratio % | E/F | g/L | mOSM | Mw | Mn | Mw/Mn |
| 0 | | | | | 0 | 0.98 | 190 | | | |
| 14.1 | 2.66 | 2.16 | 18.8 | 0 | 0 | 0.69 | 171 | 2.56 | 1.11 | 2.31 |
| 32.6 | 10.64 | 5.96 | 44.0 | 0 | 0 | 0.03 | 157 | 2.32 | 1.17 | 1.99 |
| 44.1 | 16.33 | 6.05 | 63.0 | 0 | 0 | 0 | 149 | 1.79 | 0.65 | 2.73 |
| 56.1 | 20.23 | 5.54 | 72.6 | 0 | 0 | 0 | 166 | 1.40 | 0.42 | 3.35 |
| 69.6 | 23.04 | 6.01 | 73.9 | 0 | 0 | 0 | 185 | 1.32 | 0.32 | 4.10 |
| 82.6 | 23.88 | 5.67 | 76.2 | 0 | 0 | 0 | 222 | 1.24 | 0.36 | 3.41 |
| 92.6 | 22.82 | 5.77 | 74.7 | 0 | 0 | 0 | 284 | 1.27 | 0.27 | 4.70 |

TABLE 26

Comparative Example 17:

| Culture time | DCW | RB | PHA | | 4HB | Molecular weight (×10⁵) | | Mw/Mn |
|---|---|---|---|---|---|---|---|---|
| Hr | g/L | g/L | Content % | Ratio % | E/F | Mw | Mn | |
| 0 | | | | | 0 | | | |
| 34.1 | 4.29 | 3.79 | 11.6 | 0 | 0 | 1.96 | 0.85 | 2.31 |
| 57.8 | 6.60 | 6.03 | 8.6 | 0 | 0 | 1.83 | 0.64 | 2.85 |
| 82.2 *D3 | 8.95 | 8.23 | 8.0 | 0 | 0 | 1.75 | 0.66 | 2.67 |
| 106.6 | 11.47 | 10.52 | 8.3 | 0 | 0 | 1.88 | 0.78 | 2.41 |
| 130.9 *D5 | 14.03 | 12.85 | 8.4 | 0 | 0 | 1.54 | 0.76 | 2.03 |
| 154 | 16.48 | 13.82 | 16.1 | 0 | 0 | 1.98 | 0.92 | 2.16 |

$^1$H-NMR measurement was performed by extracting PHA from the culture solution of each of *D3 and *D5

TABLE 27

| | Culture Time | Culture Termination | Carbon source | | Nitrogen source | | Added NaCl | Weight of dried bacterial cells | Bacterial cell component | PHA | 3HB | 4HB | 4HB proportion | Osmotic pressure Before culture | Molecular weight ×10⁶ | | Mw/Mn |
| | | | ECL | Fructose | Ammonium sulfate | NH4 | | | | | | | | | Mn | Mw | |
| | H | pH | g/L | g/L | g/L | g/L | g/L | g/L | g/L | wt % | wt % | wt % | mol % | mOSM | | | |
|---|---|---|---|---|---|---|---|---|---|---|---|---|---|---|---|---|---|
| Example 7 | 96 | 5.91 | 5.38 | 8.86 | 2.0 | 0.55 | | 5.01 | 3.43 | 31.5 | 26.6 | 4.9 | 15.6 | 284 | 1.16 | 5.37 | 4.6 |
| Example 8 | 96 | 5.72 | 5.38 | 8.86 | 4.0 | 1.09 | | 5.09 | 3.44 | 32.4 | 27.2 | 5.2 | 16.2 | 321 | 1.59 | 5.73 | 3.6 |
| Example 9 | 96 | 5.67 | 5.38 | 8.86 | 7.5 | 2.05 | | 4.93 | 3.32 | 32.7 | 26.7 | 6.0 | 18.4 | 373 | 1.93 | 5.69 | 3.0 |
| Example 10 | 96 | 5.93 | 5.38 | 8.86 | 10.0 | 2.73 | | 4.29 | 2.63 | 38.7 | 31.4 | 7.3 | 18.9 | 410 | 2.32 | 5.75 | 2.5 |
| Example 11 | 120 | 5.68 | 5.38 | 8.86 | 12.5 | 3.41 | | 4.93 | 2.93 | 40.6 | 30.8 | 9.9 | 24.3 | 448 | 2.29 | 5.83 | 2.5 |
| Example 12 | 120 | 6.14 | 5.38 | 8.86 | 15.0 | 4.10 | | 3.44 | 2.02 | 41.3 | 31.1 | 10.2 | 24.7 | 485 | 3.24 | 6.33 | 2.0 |
| Example 13 | 144 | 5.88 | 5.38 | 8.86 | 17.5 | 4.78 | | 4.37 | 2.64 | 39.6 | 29.6 | 10.0 | 25.2 | 518 | 2.22 | 5.46 | 2.5 |
| Example 14 | 96 | 5.86 | 5.38 | 8.86 | 2.0 | 0.55 | 0.00 | 5.21 | 3.12 | 40.2 | 34.0 | 6.2 | 15.4 | 284 | 1.33 | 4.38 | 3.3 |
| Example 15 | 96 | 5.74 | 5.38 | 8.86 | 2.0 | 0.55 | 2.50 | 5.04 | 3.14 | 37.6 | 30.5 | 7.0 | 18.7 | 369 | 1.78 | 4.85 | 2.7 |
| Example 16 | 96 | 5.91 | 5.38 | 8.86 | 2.0 | 0.55 | 5.00 | 4.05 | 2.53 | 37.4 | 28.9 | 8.5 | 22.6 | 455 | 1.61 | 5.33 | 3.3 |
| Example 17 | 96 | 6.10 | 5.38 | 8.86 | 2.0 | 0.55 | 7.50 | 2.63 | 1.69 | 35.8 | 24.8 | 11.0 | 30.8 | 540 | 2.80 | 6.06 | 2.2 |
| Example 18 | 144 | 5.89 | 5.38 | 8.86 | 2.0 | 0.55 | 10.00 | 3.90 | 2.31 | 40.9 | 28.6 | 12.3 | 30.1 | 626 | 2.42 | 5.69 | 2.3 |
| Example 19 | 96 | 5.84 | 5.38 | 8.86 | 2.0 | 0.55 | | 4.48 | 2.60 | 40.4 | 33.0 | 7.4 | 18.3 | — | 2.74 | 6.61 | 2.4 |
| Example 20 | 192 | 6.15 | 6.46 | 7.78 | 2.0 | 0.55 | | 3.97 | 2.09 | 47.3 | 34.9 | 12.4 | 26.3 | — | 3.01 | 6.50 | 2.2 |

—: Undetermined

Example 21

In the case of the flask culture using a medium, in which 5.53 g/L of δ-valerolactone and 8.86 g/L of fructose were added to the medium 1, at 30° C. and 150 rpm for four days, a PHA having Mw of 10080000, Mn of 3250000, and Mw/Mn of 3.1 was obtained.

Example 22

In the case of the flask culture using a medium, in which 5.25 g/L of δ-caprolactone and 8.86 g/L of fructose were added to the medium 1, at 30° C. and 150 rpm for four days, a PHA having Mw of 6300000, Mn of 2000000, and Mw/Mn of 3.1 was obtained.

The invention claimed is:

1. A method for producing a polyester comprising culturing a microorganism having a polyester-producing capability in a culture solution comprising a carbon source and a nitrogen source, the polyester comprising at least a 3-hydroxybutyrate unit as a polymerization unit,
wherein the produced polyester has a weight average molecular weight of 1,000,000 or greater determined by gel permeation chromatography calibrated with polystyrene standards and comprises at least the 3-hydroxybutyrate unit as the polymerization unit,
the ratio of the weight average molecular weight of the polyester to the number average molecular weight the polyester is 1.0 to 4.0, and
the culture solution has a pH of 4 to 7.5, and the culture satisfies conditions (a) and (b) below:

(a) an osmotic pressure of the culture solution is maintained from 200 mOsm to 500 mOsm during culture period; and
(b) NH₄ concentration of the culture solution is maintained at 1.20 g/L to 4.0 g/L during culture period,
wherein the microorganism is a genus *Cupriavidus*.

2. The method according to claim 1, wherein the microorganism is *Cupriavidus necator*.

3. The method according to claim 1, wherein a culture temperature is from 15° C. to 45° C.

4. The method according to claim 1, wherein the culture is a fed-batch culture or a continuous culture.

5. The method according to claim 1, wherein the carbon source comprises at least one selected from the group consisting of ε-caprolactone, δ-valerolactone, δ-caprolactone, saponified products of ε-caprolactone, δ-valerolactone and δ-caprolactone, and salts of the saponified product.

6. A method for producing a polyester,
comprising:
culturing a microorganism having a polyester-producing capability in a culture solution comprising a carbon source and a nitrogen source, the polyester comprising at least a 3-hydroxybutyrate unit as a polymerization unit, wherein the produced polyester has a weight average molecular weight of 1,000,000 or greater determined by gel permeation chromatography calibrated with polystyrene standards and comprises at least the 3-hydroxybutyrate unit as the polymerization unit, the ratio of the weight average molecular weight of the polyester to the number average molecular weight the polyester is 1.0 to 4.0, and wherein the culture solution has a pH of 4 to 7.5, the culture is a batch culture, and the culture satisfies conditions (a) and (b) below:

(a) an osmotic pressure of the culture solution at the initiation of the culture is from 200 mOsm to 700 mOsm; and
(b) $NH_4$ concentration of the culture solution at the initiation of the culture is 0.55 g/L to 4.78 g/L, wherein the microorganism is a genus *Cupriavidus*.

* * * * *